US009445857B2

United States Patent
Rogers et al.

(10) Patent No.: US 9,445,857 B2
(45) Date of Patent: Sep. 20, 2016

(54) BONE GRAFT PLACEMENT DEVICE

(75) Inventors: Jon-Paul Rogers, North Smithfield, RI (US); Timothy P. Callahan, Wrentham, MA (US); Jeffrey Wyman, Naples, FL (US); Graham Smith, Newburyport, MA (US); Daniel B. Ellis, Holliston, MA (US); Ettore Taverna, Ligornetto (CH)

(73) Assignee: Smith & Nephew, Inc., Memphis, TN (US)

( * ) Notice: Subject to any disclaimer, the term of this patent is extended or adjusted under 35 U.S.C. 154(b) by 618 days.

(21) Appl. No.: 13/606,886

(22) Filed: Sep. 7, 2012

(65) Prior Publication Data

US 2013/0066371 A1  Mar. 14, 2013

Related U.S. Application Data

(63) Continuation-in-part of application No. 13/188,254, filed on Jul. 21, 2011, now Pat. No. 9,320,557.

(60) Provisional application No. 61/532,432, filed on Sep. 8, 2011.

(51) Int. Cl.
*A61F 2/46* (2006.01)
*A61B 17/88* (2006.01)
(Continued)

(52) U.S. Cl.
CPC ....... *A61B 17/8872* (2013.01); *A61B 17/0401* (2013.01); *A61B 17/0485* (2013.01);
(Continued)

(58) Field of Classification Search
CPC .............. A61B 2017/0488; A61B 2017/0496; A61B 2017/0404; A61B 2017/06176; A61B 2017/0403; A61B 2017/0406; A61B 2017/0411; A61B 2017/0414; A61B 2017/0467; A61B 2017/0469; A61B 2017/0474; A61B 2017/0475; A61B 2017/0477; A61B 2017/0495; A61B 2017/04; A61B 2017/0401; A61B 2017/0485; A61B 2017/0487; A61B 2017/06166
See application file for complete search history.

(56) References Cited

U.S. PATENT DOCUMENTS 7,959,650 B2   6/2011  Kaiser et al.
8,100,968 B2 *  1/2012  Chan ..................... A61F 2/0811
                                              606/232

(Continued)

FOREIGN PATENT DOCUMENTS

EP         2198795      6/2010
JP      2006503655 A    2/2006
(Continued)

OTHER PUBLICATIONS

International Search Report mailed Jan. 18, 2013 in corresponding International Application No. PCT/US2012/046962.
(Continued)

*Primary Examiner* — Jonathan Miles
*Assistant Examiner* — Kendra Obu
(74) *Attorney, Agent, or Firm* — Burns & Levinson LLP; Joseph M. Maraia

(57) ABSTRACT

A surgical assembly includes a first guidewire and a second guidewire, in which each of the first guidewire and the second guidewire are configured to be received by a bone block, a first suture loop, a second suture loop, a first locking component, and a second locking component, in which the first locking component is coupled to the first suture loop and the second locking component is coupled to the second suture loop. The locking component has a hole formed therethrough, in which the hole of the locking component is configured to receive the suture, and may be tethered to a suture by knots engaging a counterbore at opposed ends of a bore defined by the hole.

10 Claims, 22 Drawing Sheets

(51) Int. Cl.
*A61B 17/04* (2006.01)
*A61B 17/16* (2006.01)
*A61B 17/82* (2006.01)
*A61B 17/86* (2006.01)
*A61B 17/00* (2006.01)
*A61B 17/17* (2006.01)
*A61B 17/06* (2006.01)
*A61F 2/40* (2006.01)

(52) U.S. Cl.
CPC ......... *A61B17/8897* (2013.01); *A61F 2/4601* (2013.01); *A61B 17/0487* (2013.01); *A61B 17/1684* (2013.01); *A61B 17/1697* (2013.01); *A61B 17/82* (2013.01); *A61B 17/864* (2013.01); *A61B 2017/00407* (2013.01); *A61B 2017/0404* (2013.01); *A61B 2017/0496* (2013.01); *A61B 2017/06176* (2013.01); *A61B 2017/1778* (2013.01); *A61F 2/4081* (2013.01)

(56) References Cited

U.S. PATENT DOCUMENTS

| | | | |
|---|---|---|---|
| 2003/0130694 A1 | 7/2003 | Bojarski et al. | |
| 2004/0186515 A1* | 9/2004 | Rosenblatt | A61B 17/0487 606/228 |
| 2005/0187577 A1 | 8/2005 | Selvitelli et al. | |
| 2007/0185532 A1 | 8/2007 | Stone et al. | |
| 2008/0039873 A1* | 2/2008 | Bonutti et al. | 606/139 |
| 2009/0192468 A1* | 7/2009 | Stone | A61B 17/0401 604/174 |
| 2009/0312776 A1 | 12/2009 | Kaiser et al. | |
| 2010/0256678 A1 | 10/2010 | Ducharme | |
| 2011/0270278 A1* | 11/2011 | Overes | A61B 17/0057 606/144 |
| 2012/0078299 A1* | 3/2012 | Ramos Clamote | 606/232 |
| 2012/0165864 A1 | 6/2012 | Hernandez et al. | |

FOREIGN PATENT DOCUMENTS

| | | |
|---|---|---|
| JP | 2009545364 A | 12/2009 |
| JP | 2010532207 A | 10/2010 |
| WO | 2004037094 | 5/2004 |

OTHER PUBLICATIONS

Taverna, E. Athroscopic Bone Graft Procedure for Anterior Inferior Glenohumeral Instability. (c) Smith & Nephew 2008.

Confidential Disclosure circ. 2011, Evidencing Contributions of Ettore Taverna MD as Inventor—Not Prior Art.

Patent Examination Report No. 1 from related Australian Application No. 2012284237 Issued Feb. 11, 2016.

Office Action from related EP Application No. 12746162.2-1654, issued May 2, 2016, 4 pages.

Notice of Reasons for Rejection from related Japanese Application No. 2014-521697 issued Jun. 13, 2016.

* cited by examiner

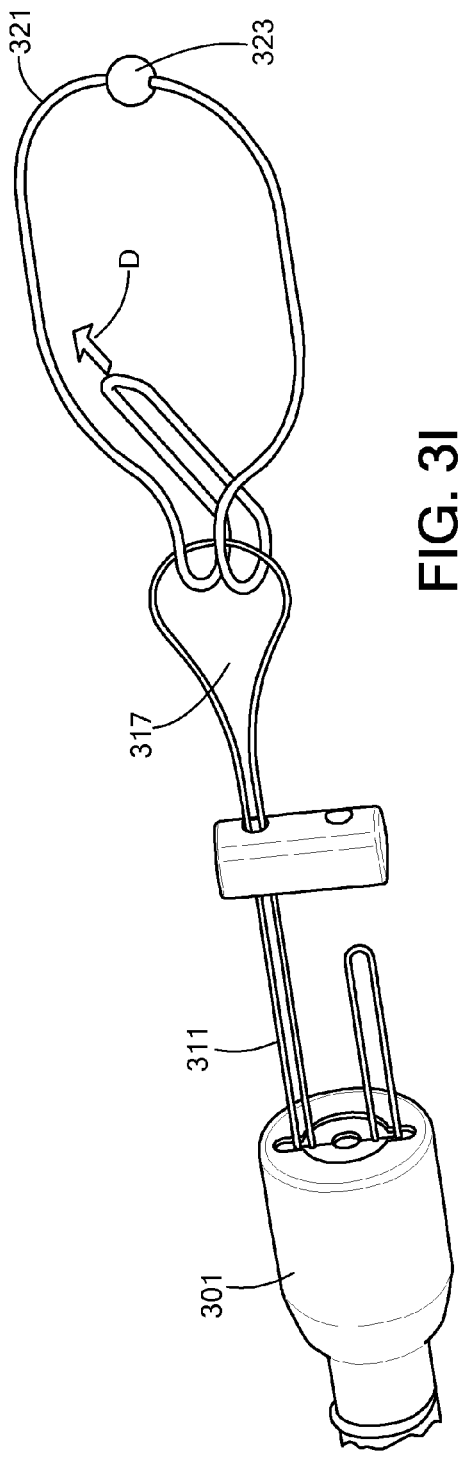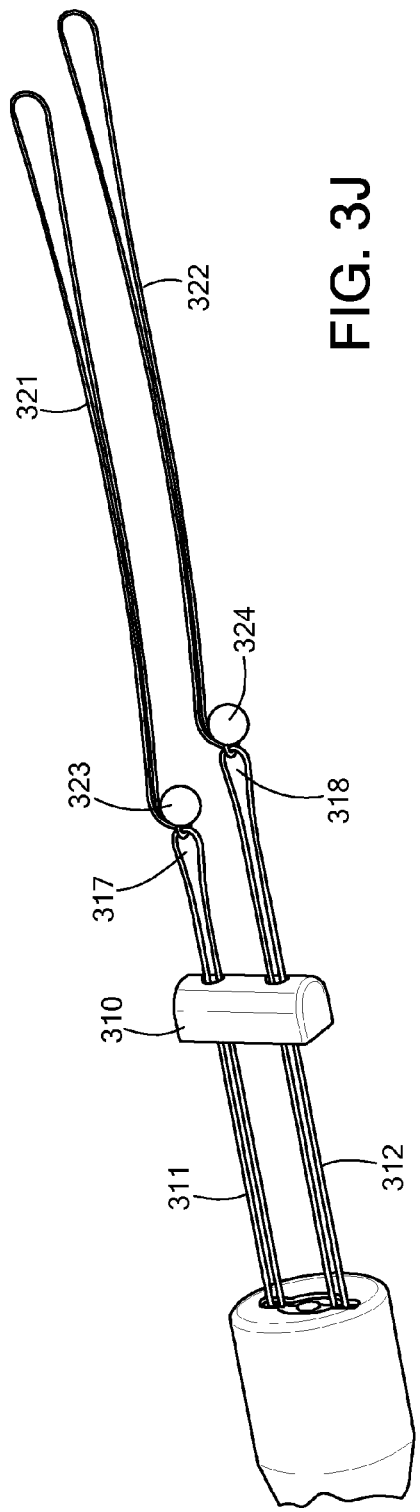

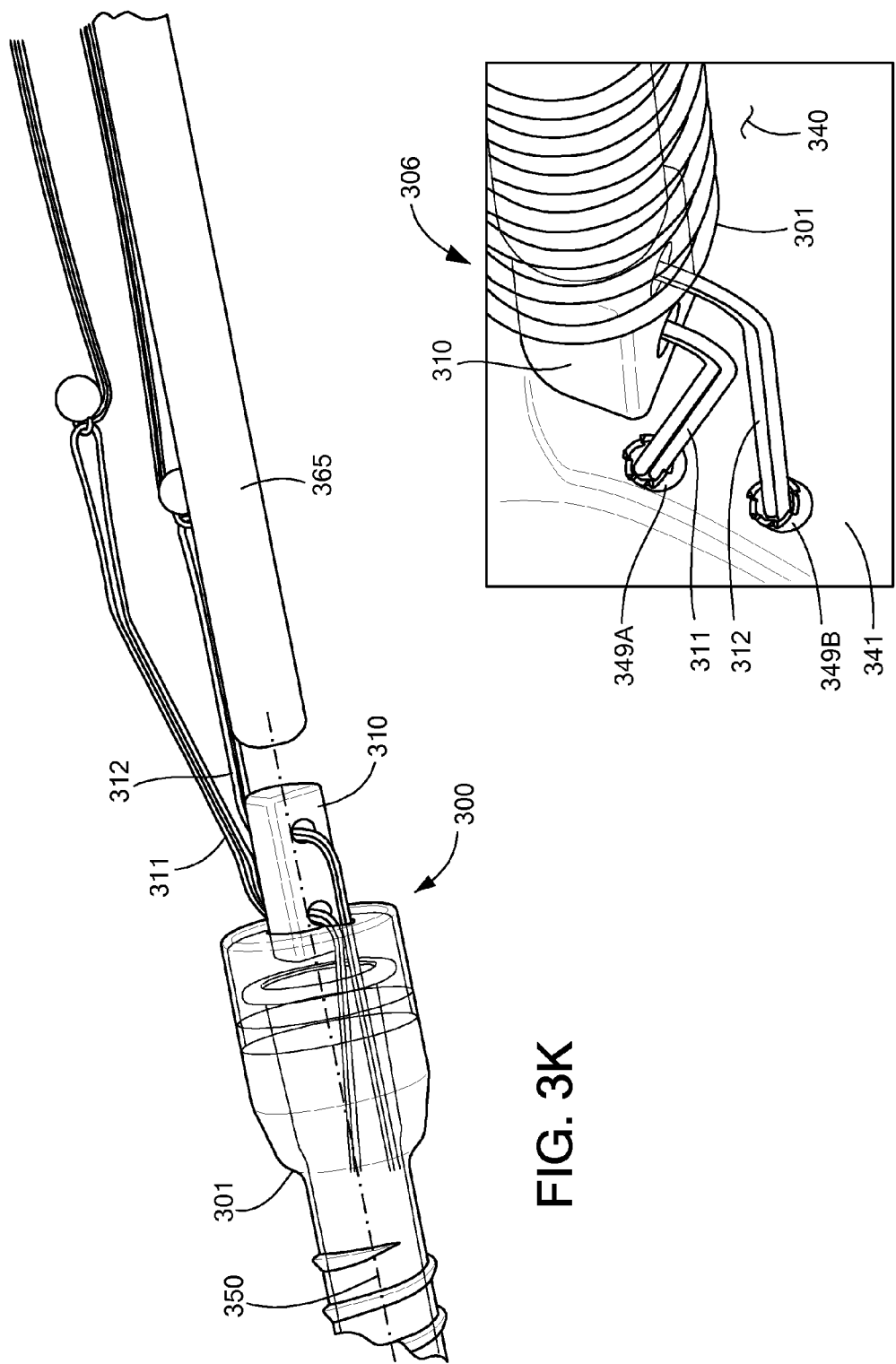

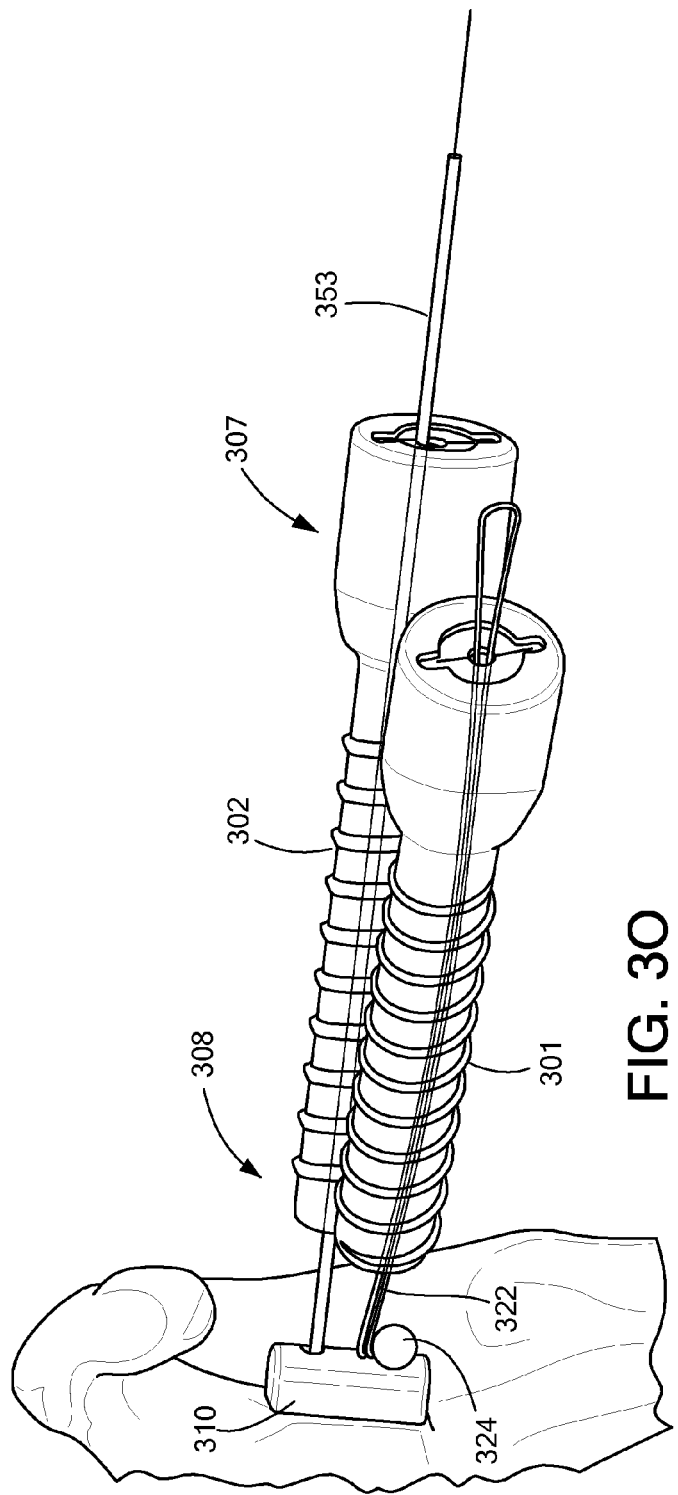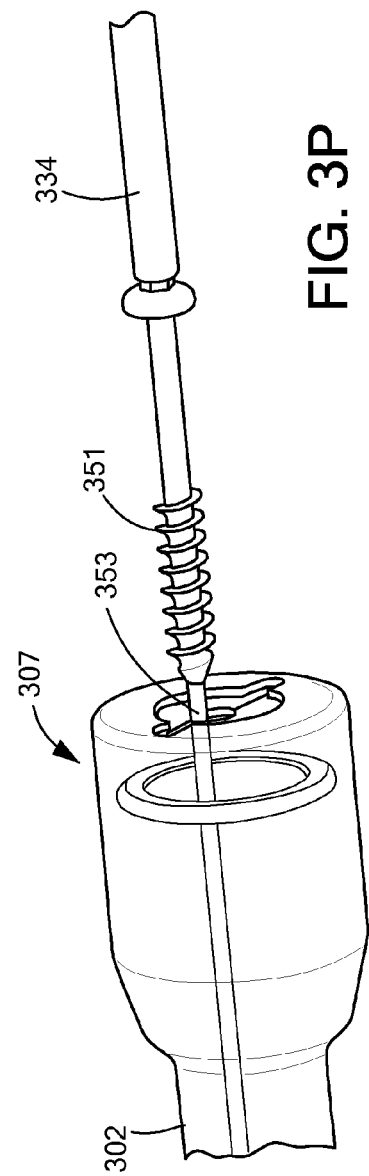
FIG. 3O
FIG. 3P

US 9,445,857 B2

BONE GRAFT PLACEMENT DEVICE

CROSS REFERENCE TO RELATED APPLICATIONS

This application is a Continuation in Part under 35 U.S.C. §120 of U.S. Utility patent application Ser. No. 13/188,254, filed Jul. 21, 2011, entitled "IMPLANT RETAINING LOOP AND GUIDE WIRE EXTENSION," and claims the benefit under 35 U.S.C. §119(e) of U.S. Provisional Patent Application No. 61/532,432, filed Sep. 8, 2011, entitled "SUTURE LOOP WITH SST BALL," the contents of which are hereby incorporated by reference in their entirety.

BACKGROUND

The etiology of anterior-inferior glenohumeral instability is multifactorial. Avulsion fractures of the anterior glenoid rim, so-called bony Bankart lesions, are associated with anterior-inferior glenohumeral instability. Successful treatment of this condition requires a surgical approach that allows relevant lesions, which may cause shoulder instability, to be identified and repaired.

Presently, anterior-inferior shoulder instability associated with lesions in soft tissue can be successfully treated arthroscopically, and the clinical outcomes may be generally similar to those found after an open procedure. However, the major risk of recurrent instability after an arthroscopic procedure, when compared to an open procedure, is related to the presence of additional bony defects of the glenoid. A present method of bony Bankart repair, or treating anterior-inferior glenohumeral instability, involves pushing/pulling a bone block with graspers within the body and securing the bone block with a suture and screws. Manipulating the bone block within the body using graspers and securing the bone block within the body using sutures may be difficult, and as a result, time-consuming, for a surgeon.

Accordingly, there exists a need for an improved technique for treating anterior-inferior glenohumeral instability.

SUMMARY

According to one aspect of the present invention, there is provided a surgical assembly, the assembly including a first guidewire, a second guidewire, in which each of the first guidewire and the second guidewire are configured to be received by a bone block, a first suture loop, a second suture loop, a first locking component, and a second locking component, in which the first locking component is coupled to the first suture loop and the second locking component is coupled to the second suture loop.

According to another aspect of the present invention, there is provided a surgical method, the method including forming a posterior portal in a body, forming an anterior portal in the body, inserting a first guidewire and a second guidewire into the posterior portal, pulling each of the first guidewire and the second guidewire out of the body, through the anterior portal, disposing each of the first guidewire and the second guidewire through a bone block, securing a first suture loop to the first guidewire and a second suture loop to the second guidewire, disposing the bone block into the body with the first guidewire and the second guidewire, through the anterior portal, removing each of the first suture loop and the second suture loop, and securing the bone block within the body, against the glenoid.

According to another aspect of the present invention, there is provided a surgical kit, the kit including a first cannula having a hole formed therethrough and configured to receive a bone block, a proximal end, a distal end, and a central axis defined therethrough, a first guidewire, a second guidewire, a first suture loop comprising a first locking member, and a second suture loop comprising a second locking member.

According to another aspect of the present invention, there is provided a method for forming a closed loop for a surgical delivery apparatus, the method including providing a suture and a locking component, the locking component having a hole formed therethrough and is configured to receive the suture, disposing a first end of the suture through the hole formed through the locking component in a first direction, disposing a second end of the suture through the hole formed through the locking component in a second direction that is opposite to the first direction, forming a first knot on the suture with the first end of the suture, and forming a second knot on the suture with the second end of the suture.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The following is directed to various exemplary embodiments of the disclosure. Although one or more of these embodiments may be preferred, the embodiments disclosed should not be interpreted, or otherwise used, as limiting the scope of the disclosure, including the claims. In addition, those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims refer to particular features or components. As those having ordinary skill in the art will appreciate, different persons may refer to the same feature or component by different names. This document does not intend to distinguish between components or features that differ in name but not function. The figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component is coupled to a second component, that connection may be through a direct connection, or through an indirect connection via other components, devices, and connections. Further, the terms "axial" and "axially" generally mean along or substantially parallel to a central or longitudinal axis, while the terms "radial" and "radially" generally mean perpendicular to a central, longitudinal axis.

Additionally, directional terms, such as "above," "below," "upper," "lower," etc., are used for convenience in referring to the accompanying drawings. In general, "above," "upper," "upward," and similar terms refer to a direction toward the earth's surface from below the surface along a borehole, and "below," "lower," "downward," and similar terms refer to a direction away from the surface along the borehole, i.e., into the borehole, but is meant for illustrative purposes only, and the terms are not meant to limit the disclosure.

Figure 1:
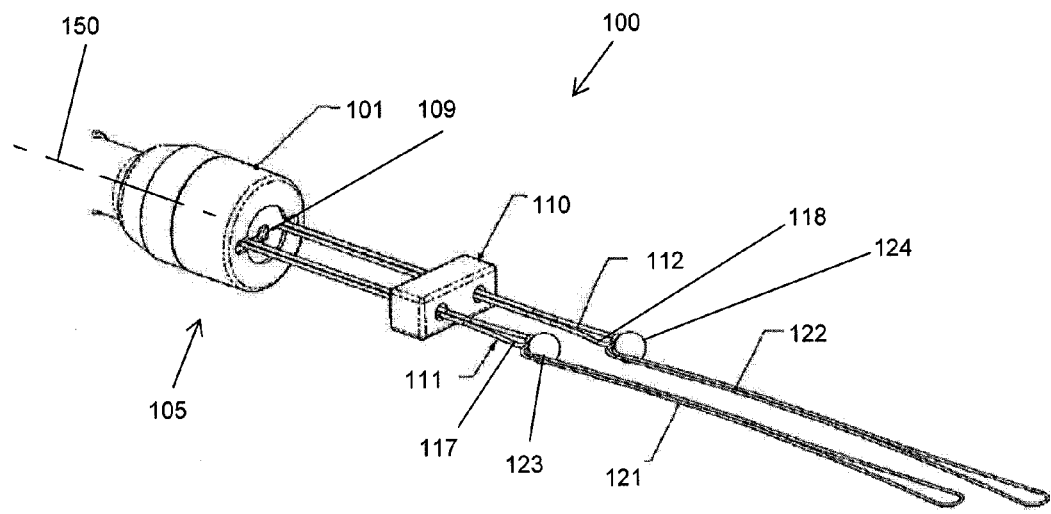
FIG. 1 shows a perspective view of a surgical assembly according to embodiments disclosed herein.

Referring now to FIG. 1, a perspective view of a surgical assembly 100, in accordance with embodiments disclosed herein, is shown. In one or more embodiments, the assembly 100 may include a first cannula 101, a first guidewire 111, a second guidewire 112, a first suture loop 121, a second suture loop 122, a first locking member 123, and a second locking member 124. As shown, each of the first guidewire 111 and the second guidewire 112 are configured to be received by a bone block 110. Further, as shown, the first locking component 123 is coupled to the first suture loop 121 and the second locking component 124 is coupled to the second suture loop 122.

In one or more embodiments, the first cannula 101 may include a hole 109 formed therethrough, a proximal end 105, a distal end (not shown), and a central axis 150 defined therethrough. In one or more embodiments, the hole 109 of the first cannula 101 may be configured to receive a bone block/graft, e.g., the bone block 110. As will be discussed below, in one or more embodiments, the first guidewire 111 and the second guidewire 112 may be used to reposition, or reorient, the bone block 110 such that the bone block 110 may be disposed within the hole 109 of the first cannula 101 and displaced through the first cannula 101. For example, in one or more embodiments, the bone block 110 may be repositioned, or reoriented, by the first guidewire 111 and the second guidewire 112 such that a longitudinal axis of the bone block 110 is substantially parallel with the central axis 150 of the first cannula 101. Further, the first guidewire 111 and the second guidewire 112 may be used to move, or displace, the bone block 110 through the first cannula 101, into a body (not shown).

In one or more embodiments, each of the first guidewire 111 and the second guidewire 112 may be formed from any substantially rigid material or any flexible material known in the art. For example, each of the first guidewire 111 and the second guidewire 112 may be made of a plastic or a metal, such as Nitinol. Further, in one or more embodiments, each of the first guidewire 111 and the second guidewire 112 may be looped guidewires. In other words, in one or more embodiments, the first guidewire 111 may include a first loop 117 and the second guidewire 112 may include a second loop 118. In one or more embodiments, the first loop 117 of the first guidewire 111 and the second loop 118 of the second guidewire 112 may be configured to receive suture loops 121, 122, respectively. Although FIG. 1 shows an embodiment of the surgical assembly 100 with only two guidewires 111, 112, those having ordinary skill in the art will appreciate that more or less than two guidewires may be used. For example, in one or more embodiments, one, three, four, or more guidewires may be used.

In one or more embodiments, the first suture loop 121 may be configured to be secured to the first guidewire 111 and the second suture loop 122 may be configured to be secured to the second guide wire 112. For example, as shown, the first suture loop 121 is configured to be secured to the first loop 117 of the first guidewire 111 and the second suture loop 122 is configured to be secured to the second loop 118 of the second guidewire 112. As will be discussed below, in one or more embodiments, the first suture loop 121 may be displaced, looped or passed, through the first loop 117 of the first guidewire 111, and also displaced, looped or passed, back through itself in order to secure the first suture loop 121 and the first locking member 123 to the first loop 117 of the first guidewire 111. Similarly, the second suture loop 122 may be displaced, looped or passed, through the second loop 118 of the second guidewire 112, and also displaced, looped or passed, back through itself in order to secure the second suture loop 122 and the second locking member 124 to the second loop 118 of the second guidewire 112. In one or more embodiments, in order to remove, or disengage, each of the first suture loop 121 and the second suture loop 122 from the first guidewire 111 and the second guidewire 112, respectively, a surgeon may pull each of the first locking member 123 and the second locking member 124 in a direction that is substantially away from each of the guidewires 111, 112. Pulling each of the first locking member 123 and the second locking member 124 in a direction that is substantially away from each of the guidewires 111, 112 may cause each of the suture loops 121, 122 to become unraveled, or become un-looped, and disengaged from each of the guidewires 111, 112.

Further, in one or more embodiments, each of the first suture loop 121 and the second suture loop 122 may be formed from any flexible material known in the art, such as suture, plastic, or a malleable metal, such as Nitinol. Alternatively, varying arrangements of holes for suture loops may be employed, such as one or multiple (3 or more) suture loops may be employed. In one or more embodiments, each of the first suture loop 121 and the second suture loop 122 may be a closed, continuous loop. Alternatively, in one or more embodiments, each of the first suture loop 121 and the second suture loop 122 may be closed and may contain a knot (not shown).

As discussed above, in one or more embodiments, the first locking component 123 may be coupled to the first suture loop 121 and the second locking component 124 may be coupled to the second suture loop 122. Those having ordinary skill in the art will appreciate that the first locking component 123 and the second locking component 124 may be coupled to the first suture loop 121 and the second suture loop 122, respectively, by any means known in the art. For example, the first locking component 123 and the second locking component 124 may be coupled to the first suture loop 121 and the second suture loop 122, respectively, by mechanical or chemical means, such as crimping, molding, or gluing. Alternatively, in one or more embodiments, each of the first locking component 123 and the second locking component 124 may include a hole formed therethrough, in which each of the first locking component 123 and the second locking component 124 may be threaded onto the first suture loop 121 and the second suture loop 122, respectively, e.g., a bead on a necklace. As shown, each of the first locking component 123 and the second locking component 124 is substantially spherical in shape. Those having ordinary skill in the art will appreciate that the shape of the first locking component 123 and the second locking component 124 may be any shape known in the art. For example, the shape of each of the first locking component 123 and the second locking component 124 may be spherical, hemi-spherical, cubic, prismatic, pyramidal, or any other shape known in the art. Further, each of the first locking component 123 and the second locking component 124 may be formed from any material known in the art. For example, in one or more embodiments, each of the first locking component 123 and the second locking component 124 may be formed from metal, plastic, ceramic, or any other material known in the art. Alternatively, each of the first locking component 123 and the second locking component 124 may be formed form any biocompatible and/or bioabsorbable material known in the art.

Referring to FIGS. 2A-2F, multiple views of a surgical assembly 200, in accordance with embodiments disclosed herein, are shown. In one or more embodiments, the assembly 200 may include a first cannula 201, a first guidewire 211, a second guidewire 212, a first suture loop 221, a second suture loop 222, a first locking member 223, and a second locking member 224.

Figure 2A:
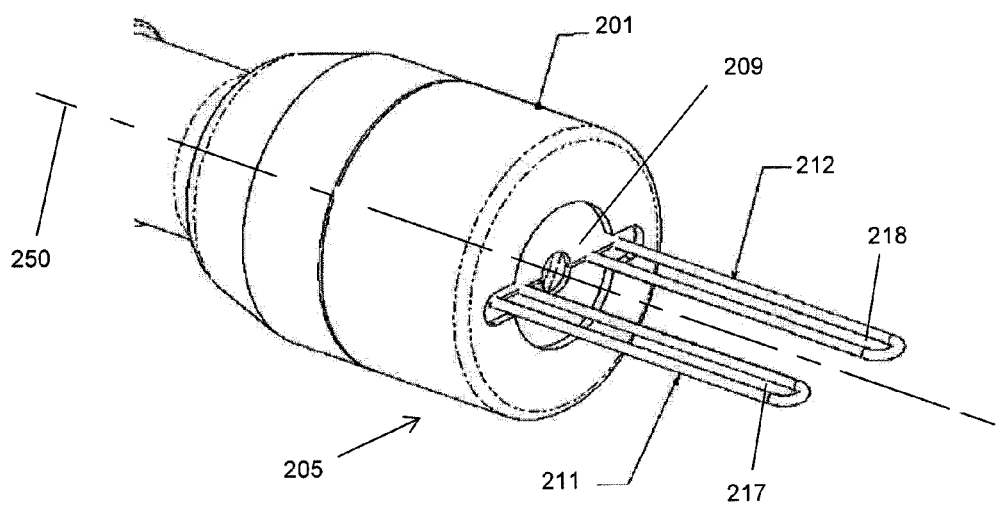
FIGS. 2A-2F show multiple views of a surgical assembly according to embodiment disclosed herein.

As shown in FIG. 2A, the first cannula 201 includes a hole 209 formed therethrough, a proximal end 205, a distal end (not shown), and a central axis 250 defined therethrough is shown. In one or more embodiments, each of the first guidewire 211 and the second guidewire 212 may be disposed within, or inserted into, the first cannula 201 through an end of the first cannula, e.g., the distal end, and displaced through the first cannula 201, and may exit through the proximal end 205 of the first cannula 201. As discussed above, each of the first guidewire 211 and the second guidewire 212 may be formed from any substantially rigid material or any flexible material known in the art. For example, each of the first guidewire 211 and the second guidewire 212 may be made of a plastic or a metal, such as Nitinol. Further, in one or more embodiments, each of the first guidewire 211 and the second guidewire 212 may be looped guidewires. In other words, as shown, the first guidewire 211 may include a first loop 217 and the second guidewire 212 may include a second loop 218.

Figure 2B:
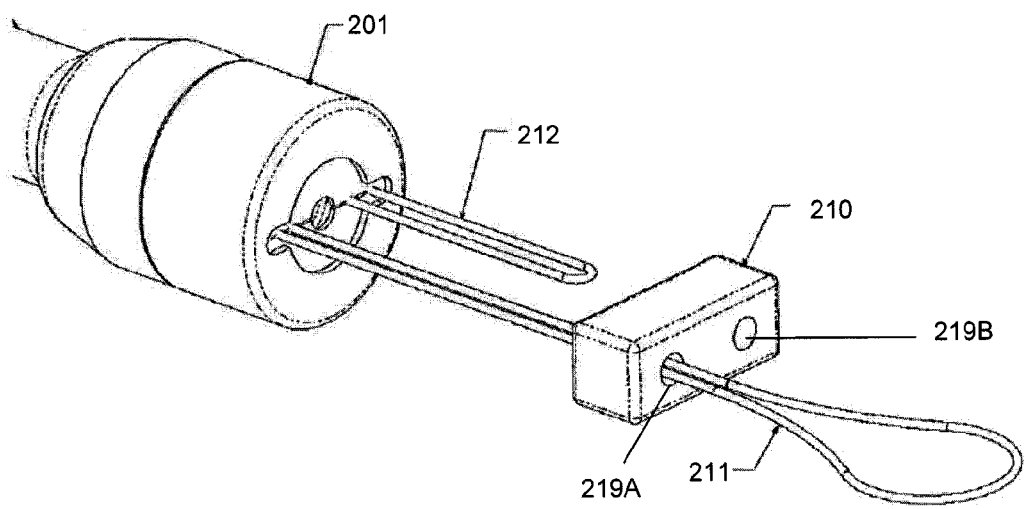

As shown in FIG. 2B, the first guidewire 211 may be disposed through the first cannula 201 and through a bone block 210. As shown, the bone block 210 includes two holes 219A, 219B, which are configured to receive the first guidewire 211 and the second guidewire 212, respectively. Those having ordinary skill in the art will appreciate that the bone block 210 may be any bone block or bone graft that may be used in a surgical procedure. For example, in one or more embodiments, the bone block 210 may be used to treat anterior inferior glenohumeral instability within a body. Alternatively, the bone block 210 may be a bone block or bone graft of an appropriate size and shape, e.g. of appropriate dimensions, that may be used in a surgical procedure involving the shoulder, hip, knee, wrist, or ankle in a body, such as a labrum repair.

Figure 2C:
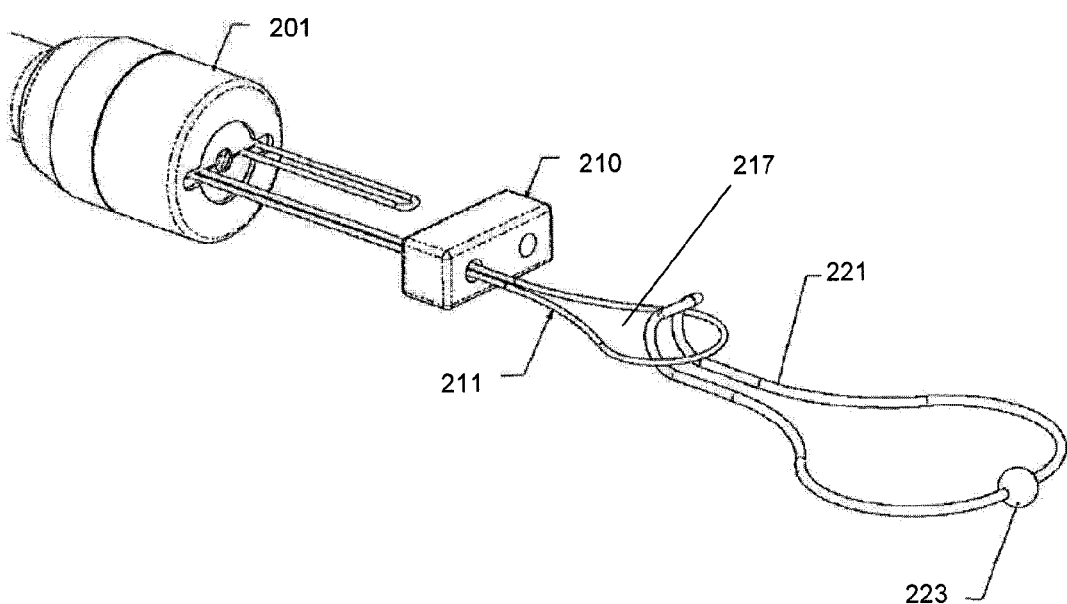

As shown in FIG. 2C, once the first guidewire 211 has been disposed through the bone block 210, the first suture loop 221 may be displaced, looped or passed, through the first loop 217 of the first guidewire 211. Further, as shown, the first locking component 223 is coupled to the first suture loop 221. As discussed above, in one or more embodiments, the first locking component 223 may be coupled to the first suture loop 221. Those having ordinary skill in the art will appreciate that the first locking component 223 may be coupled to the first suture loop 221, by any means known in the art. For example, the first locking component 223 may be coupled to the first suture loop by suitable mechanical or chemical means, such as crimping, molding, welding or gluing. Alternatively, in one or more embodiments, the first locking component 223 may include a hole formed therethrough, in which the first locking component 223 may be threaded onto the first suture loop 221, e.g., a bead on a necklace.

Figure 2D:
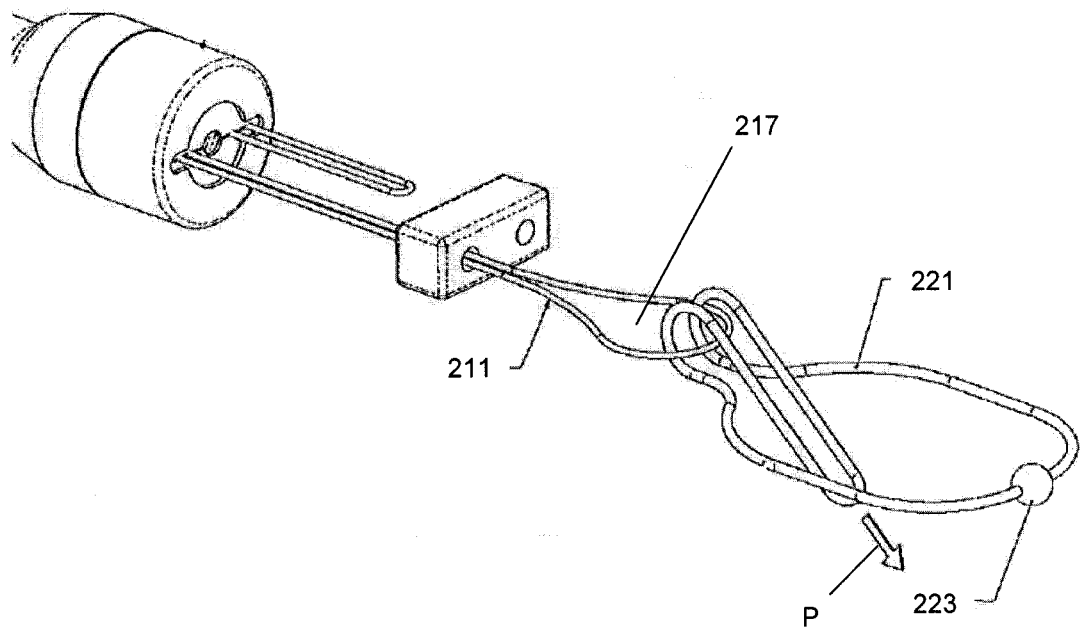

As shown in FIG. 2D, the first suture loop 221 may be also displaced, looped or passed, back through itself, e.g., in the direction of arrow P, in order to secure the first suture loop 221 and the first locking member 223 to the first loop 217 of the first guidewire 211. As discussed above, in one or more embodiments, the first suture loop 221 may be formed from any flexible material known in the art, such as suture, plastic, or a malleable metal, such as Nitinol. In one or more embodiments, the first suture loop 221 may be a closed, continuous loop. Alternatively, in one or more embodiments, the first suture loop 221 may be closed and may contain a knot (not shown).

Figure 2E:
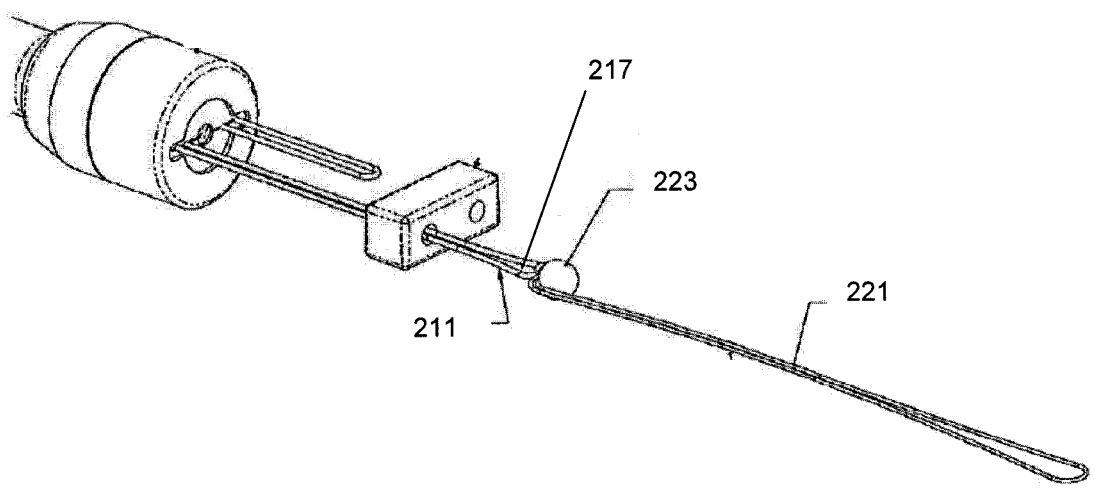

As shown in FIG. 2E, once the first suture loop 221 is displaced, looped or passed, through the first loop 217 of the first guidewire 211 and also displaced, looped or passed, back through itself, the first suture loop 221 may be tensioned, e.g., substantially in the direction of the arrow P of FIG. 2D, to secure the first suture loop 221 and the first locking member 223 to the first guidewire 211. Those having ordinary skill in the art will appreciate that the first suture loop 221 may be secured to the first guidewire 211 by other methods known in the art, other than what is described above. For example, the first suture loop 221 may be tied in a knot to the first guidewire 211. Alternatively, the first suture loop 221 may be displaced, looped or passed, through the first loop 217 of the first guidewire 211, and an end of the first suture loop 221 may be wrapped, or twisted, around an opposite end of the first suture loop 221 in order to secure the first suture loop 221 to the first guidewire 211. Further, as discussed above, in one or more embodiments, in order to remove, or disengage, the first suture loop 221 from the first guidewire 211, a surgeon may pull the first locking member 223 in a direction that is substantially away from the first guidewire 211. Pulling the first locking member 223 in a direction that is substantially away from the first guidewire 211 may cause the first suture loop 221 to become unraveled, or become un-looped, and disengaged from the first guidewire 211.

Figure 2F:
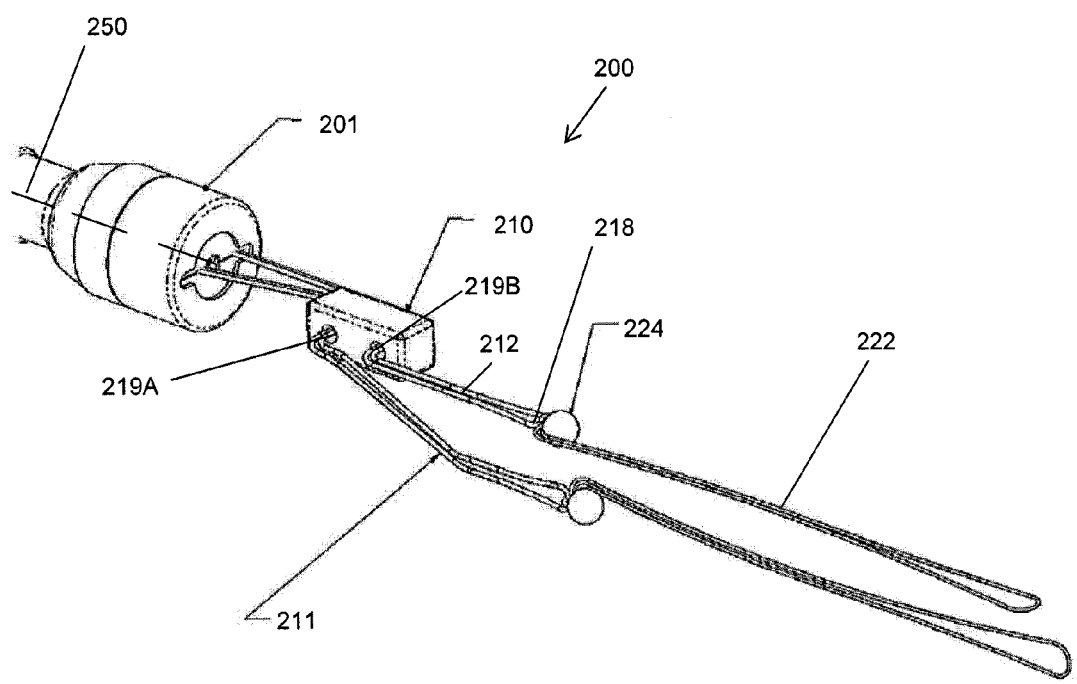

Referring now to FIG. 2F, a perspective view of the assembly 200, in accordance with embodiments disclosed herein, is shown. As shown, the same procedure, shown and described above in FIGS. 2B-2E with regard to the first guidewire 211 and the first suture loop 221, may be applied to the second guidewire 212 and the second suture loop 222. For example, in one or more embodiments, the second guidewire 212 may be disposed through the hole 219B of the bone block 210. Further, in one or more embodiments, the second suture loop 222 may be displaced, looped or passed, through the second loop 218 of the second guidewire 212. Furthermore, in one or more embodiments, the second suture loop 222 may be also displaced, looped or passed, back through itself, e.g., in the direction of the arrow P of FIG. 2D, in order to secure the second suture loop 222 and the second locking member 224 to the second loop 218 of the second guidewire 212. Moreover, in one or more embodiments, once the second suture loop 222 is displaced, looped or passed, through the second loop 218 of the second guidewire 212 and also displaced, looped or passed, back through itself, the second suture loop 222 may be tensioned, e.g., substantially in the direction of the arrow P of FIG. 2D, to secure the second suture loop 222 and the second locking member 224 to the second guidewire 212. As discussed above, the bone block 210 may be repositioned, or reoriented, by the first guidewire 211 and the second guidewire 212 such that a longitudinal axis of the bone block 210 is substantially parallel with the central axis 250 of the first cannula. Further, the first guidewire 211 and the second guidewire 212 may be used to move, or displace, the bone block 210 through the first cannula 201.

A surgical method, in accordance with embodiments disclosed herein, may include forming a posterior portal in a body, forming an anterior portal in the body, inserting a first guidewire and a second guidewire into the posterior portal, pulling each of the first guidewire and the second guidewire out of the body, through the anterior portal, disposing each of the first guidewire and the second guidewire through a bone block, securing a first suture loop to the first guidewire and a second suture loop to the second guidewire, disposing the bone block into the body with the first guidewire and the second guidewire, through the anterior portal, removing each of the first suture loop and the second suture loop, and securing the bone block within the body, against the glenoid.

In one or more embodiments, disposing the bone block into the body may include orienting the bone block such that a longitudinal axis of the bone block is substantially parallel to the central axis of the first cannula. In one or more embodiments, pulling each of the first guidewire and the second guidewire out of the body may include using a grasper to pull each of the first guidewire and the second guidewire out of the body, through the anterior portal. Further, in one or more embodiments, disposing the bone block into the body may include pushing the bone block into the body, through the first cannula, with an obturator. In one or more embodiments, disposing the bone block into the body may include pulling the bone block into the body, through the first cannula, with each of the first guidewire and the second guidewire. Furthermore, in one or more embodiments, securing the bone block within the body comprises securing at least one threaded screw through the bone block, into the glenoid.

The method may also include disposing a guide comprising a hook into the body, through the posterior portal, positioning the hook of the guide on an anterior side of the glenoid, forming a first hole and a second hole through the glenoid, from the posterior side of the glenoid to the anterior side of the glenoid, inserting a first cannula into the body, through the anterior portal, the first cannula comprising a hole formed therethrough, a proximal end, a distal end, and a central axis defined therethrough, and removing each of the first guidewire and the second guidewire from the body.

Figure 3A:
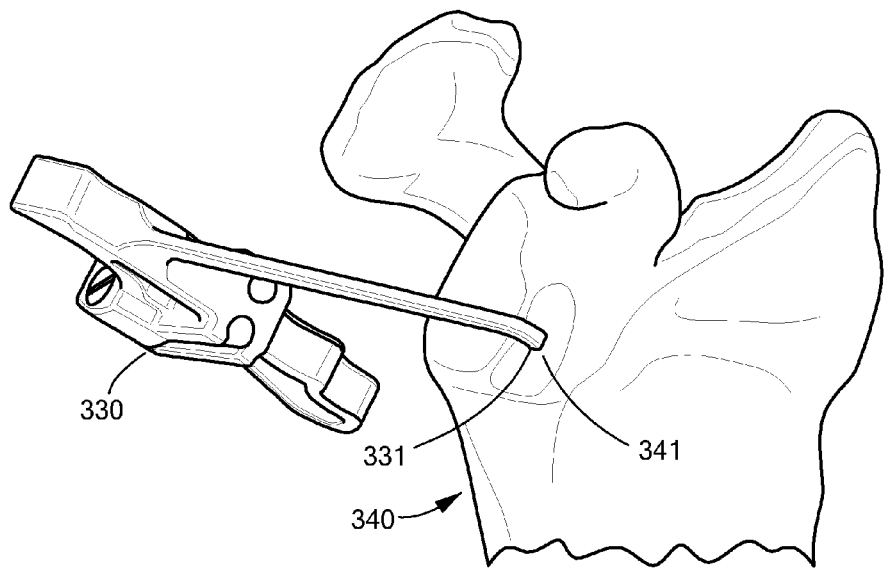
FIGS. 3A-3R show a method of using a surgical assembly within a body according to embodiments disclosed herein.
Figure 3B:
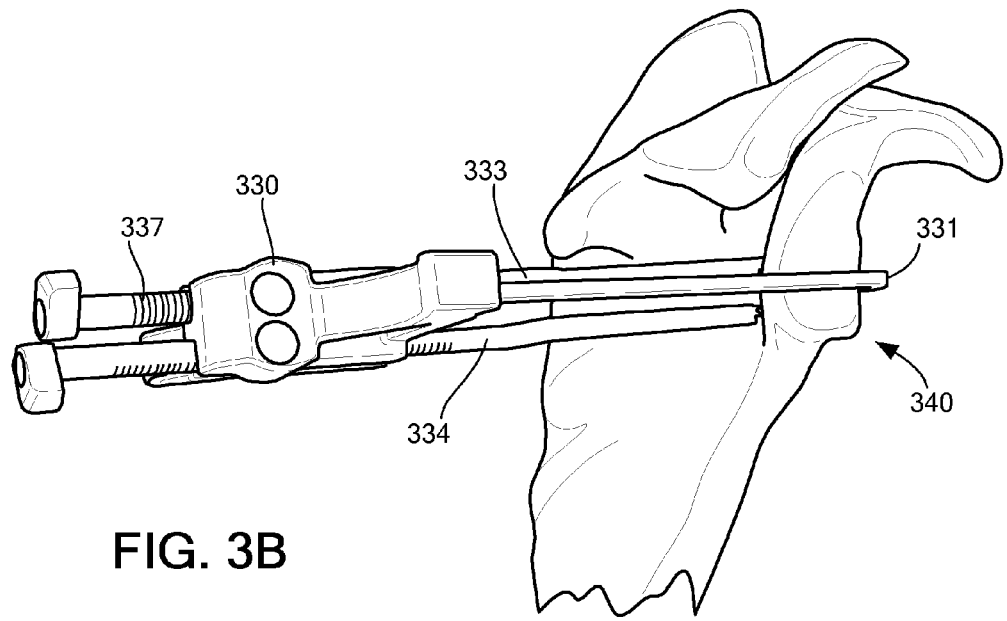
Figure 3C:
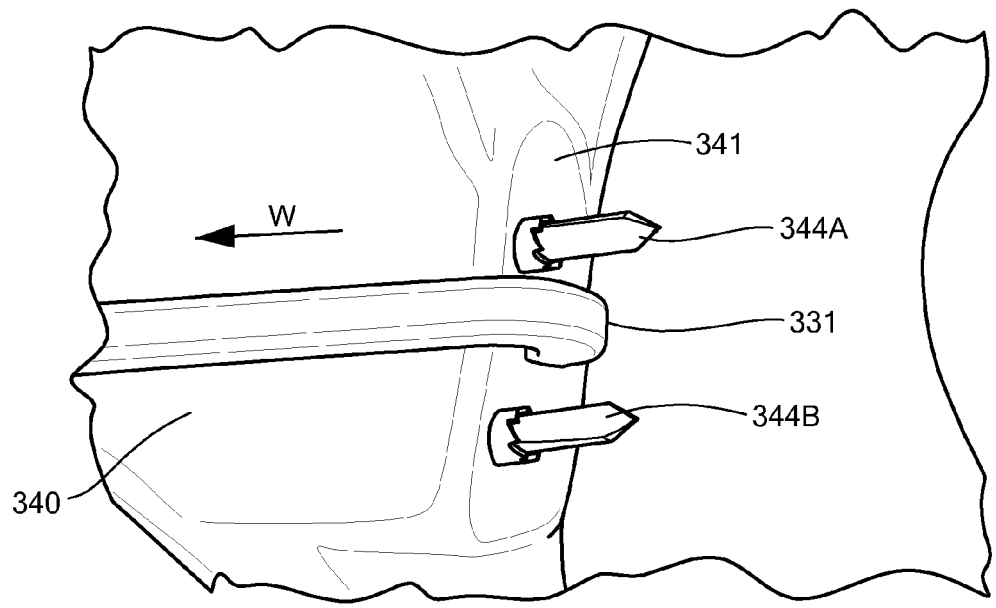
Figure 3D:
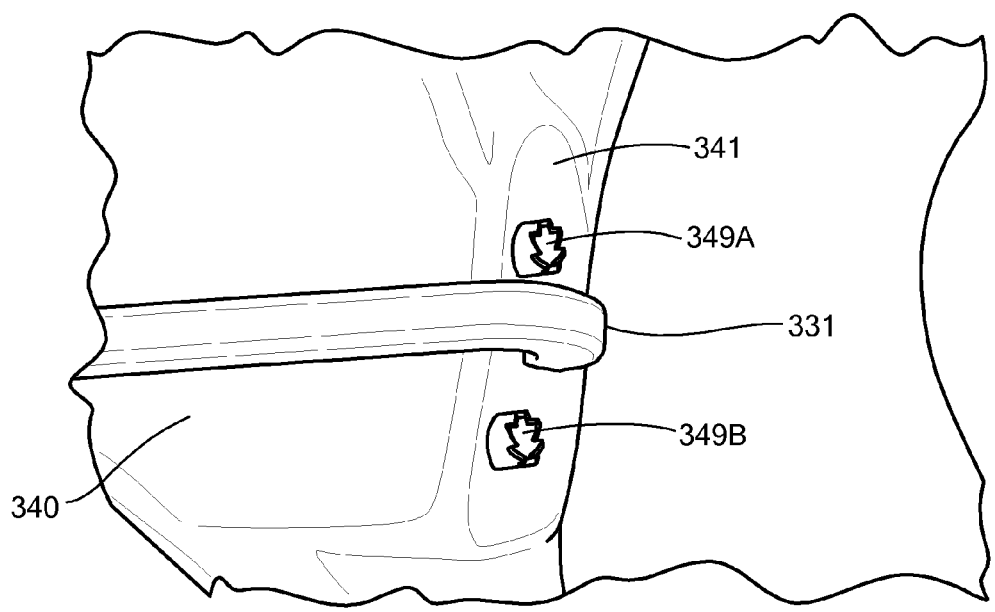
Figure 3E:
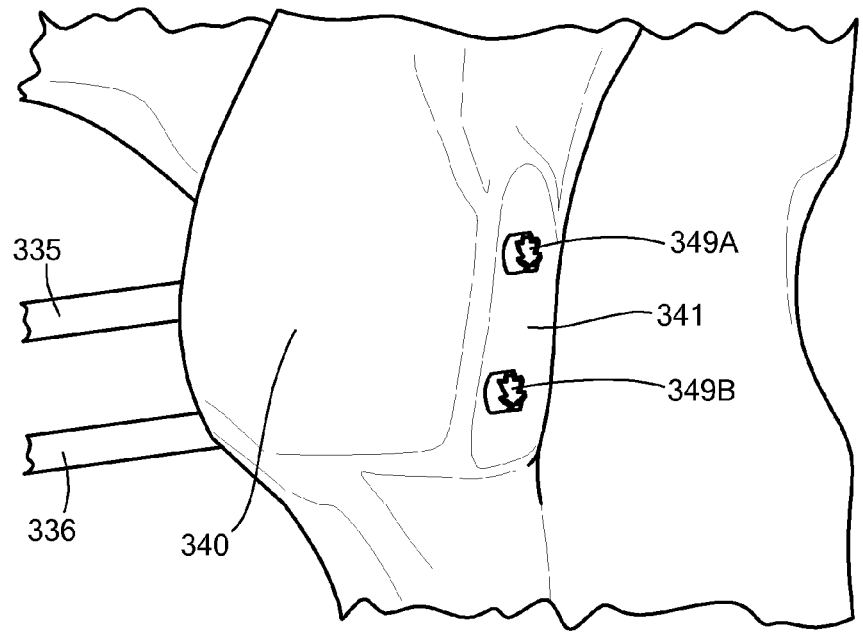
Figure 3F:
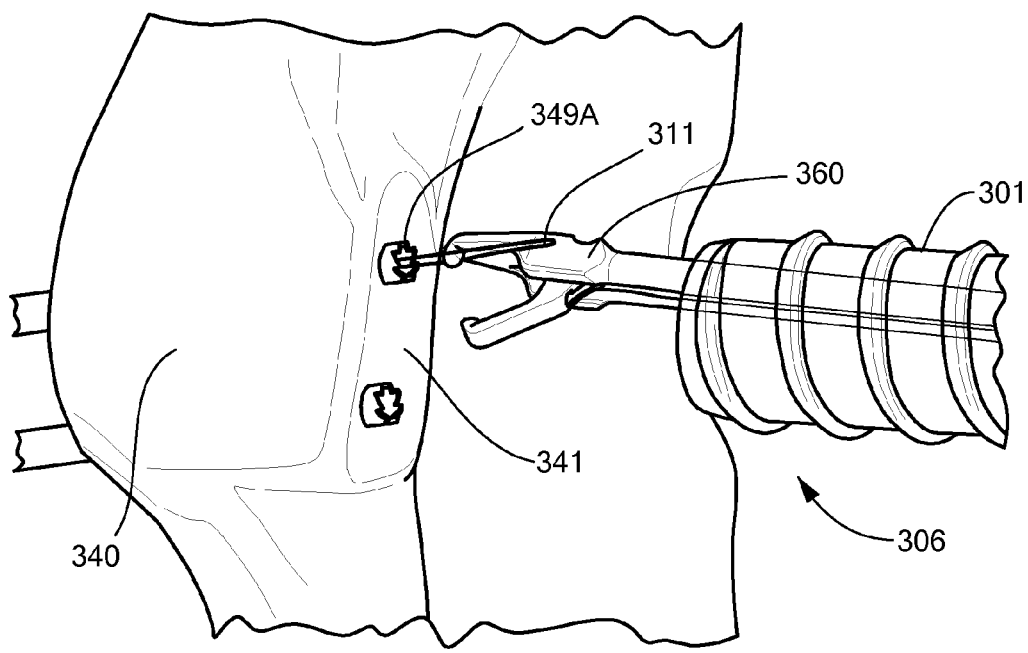
Figure 3G:
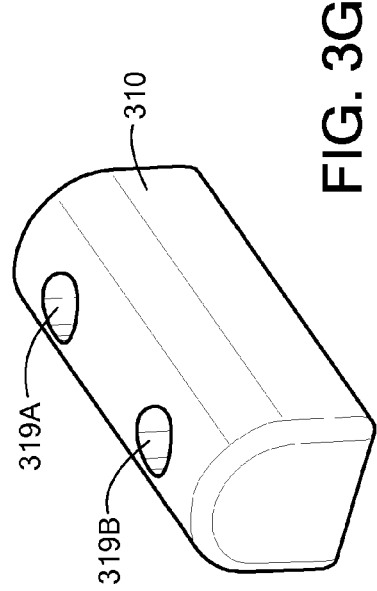
Figure 3H:
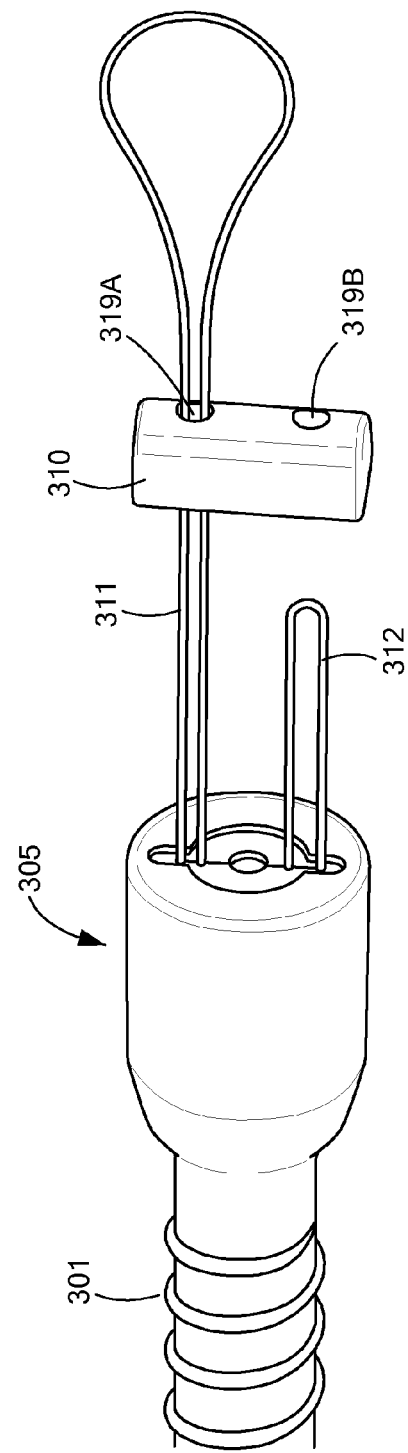
Figure 3M:
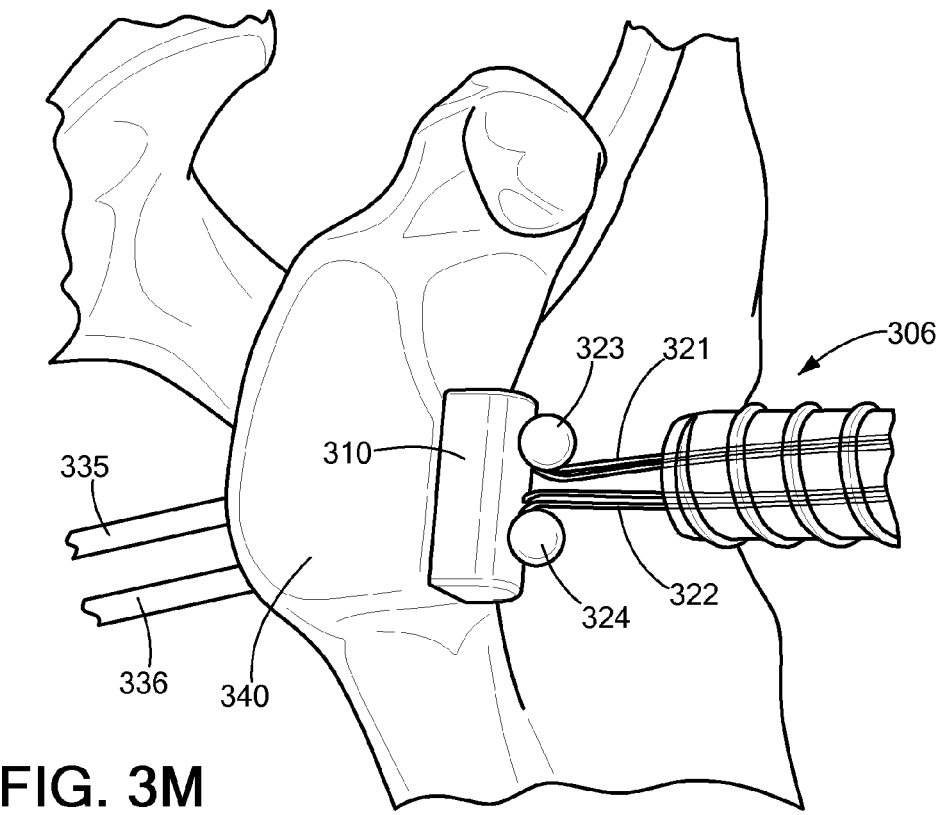
Figure 3N:
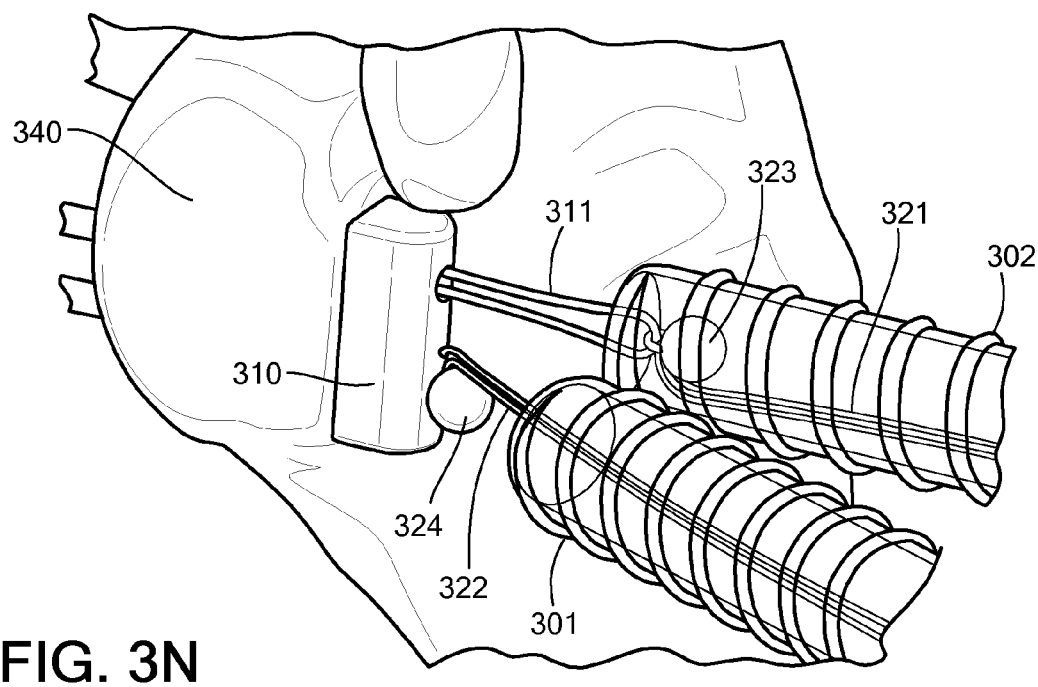
Figure 3Q:
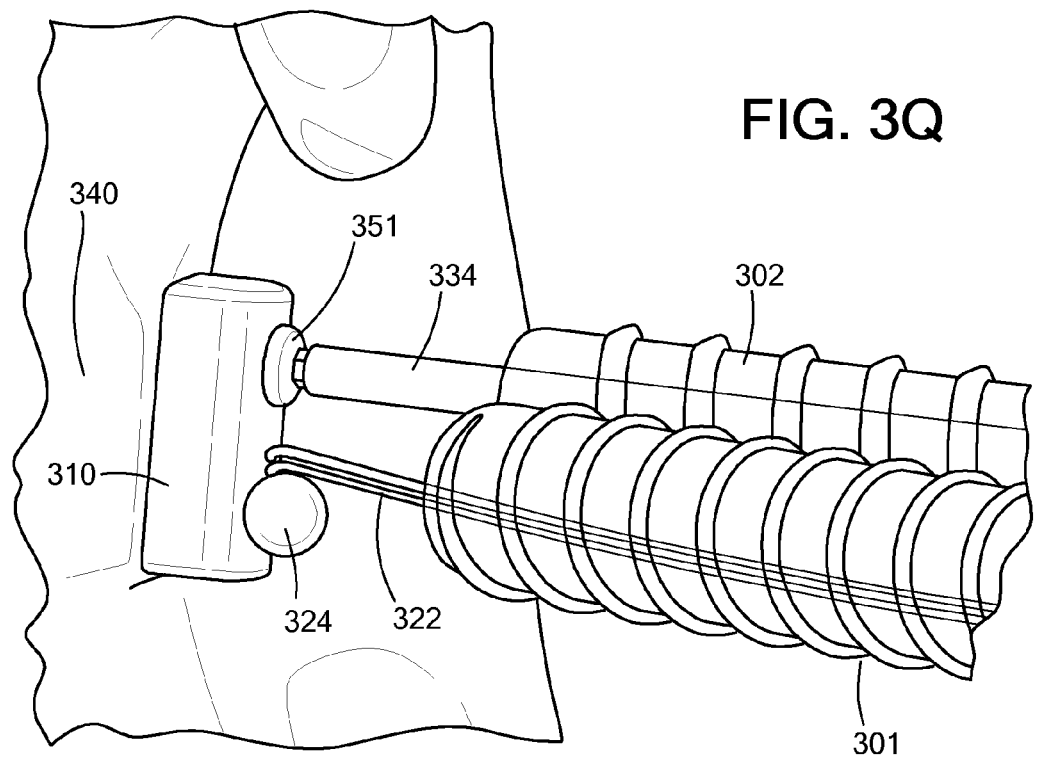
Figure 3R:
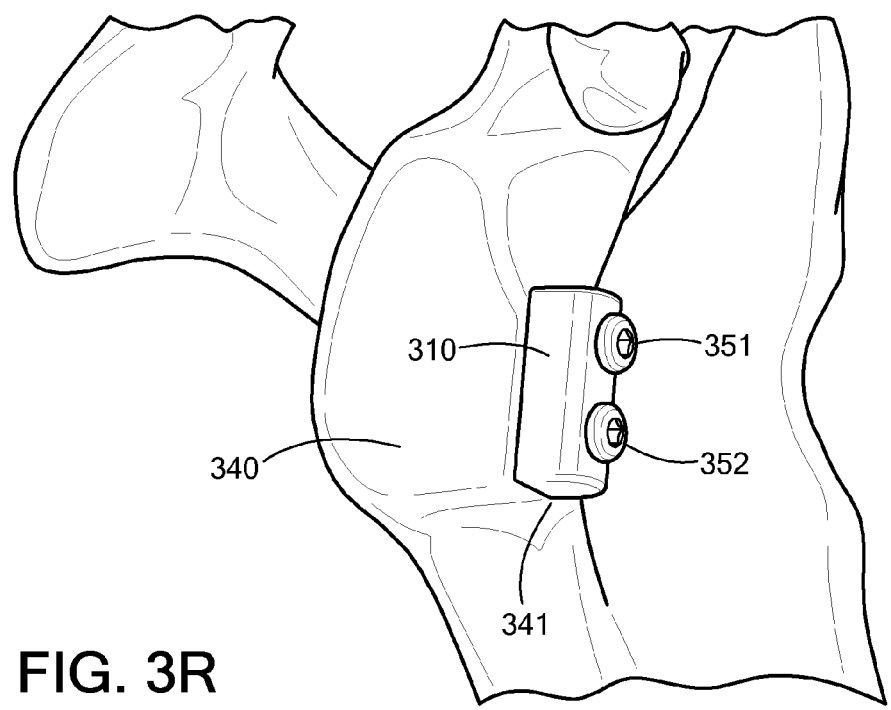

For example, referring now to FIGS. 3A-3R, a surgical method, in accordance with embodiments disclosed herein, is shown. In one or more embodiments, a surgical assembly 300 may include a first cannula 301, a first guidewire 311, a second guidewire 312, a first suture loop 321, a second suture loop 322, a first locking member 323, and a second locking member 324.

Referring to FIG. 3A, a spinal needle (not shown) may be inserted from a posterior side of a glenoid 340 to an anterior side of the glenoid 340, along a face of the glenoid 340. According to one or more aspects, the spinal needle may be positioned below an equator (not shown) of the glenoid 340 and may be used to confirm placement of a posterior instrument portal (not shown). Once the posterior instrument portal is formed, a hooked end 331 of a glenoid guide 330 may be disposed within, or inserted through, the posterior instrument portal. The hooked end 331 of the glenoid guide 330 may be passed across the glenoid 340 and over an anterior edge 341 of the glenoid 340, substantially parallel to the glenoid face in order to avoid damaging the articular surface. The glenoid guide 330 may be rotated such that the hooked end 331 of the glenoid guide 330 may engage the anterior edge 341 of the glenoid 340. The hooked end 331 of the glenoid guide 330 may be placed at the 4 o'clock position and may correlate with a midpoint of a bone block (not shown). However, those having ordinary skill in the art will appreciate that the hooked end 331 of the glenoid guide 330 may be placed at any position on the glenoid 340. For example, the hooked end 331 of the glenoid guide 330 may be placed at the 2 o'clock position and may correlate with the midpoint of the bone block.

Referring to FIG. 3B, once the hooked end is positioned, a first guide 333 may be placed in a superior hole (not shown) of the glenoid guide 330. A skin incision may be made and the first guide 333 may be advanced into the body until the first guide 333 engages a posterior side of the glenoid 340. The first guide 333 may include ratchet teeth 337, or threads, that may engage with corresponding ratchet threads, or threads, of the glenoid guide 330. According to one or more aspects, the first guide 333 may be advanced, displaced, and/or secured into the body, along the glenoid guide 330 using the ratchet teeth 337. Similarly, a second guide 334 may also be disposed into the body and may also engage a posterior side of the glenoid 340. According to one or more aspects, the second guide 334 may be placed in an inferior hole (not shown) of the glenoid guide 330. Further, a first sleeve (not shown) and a second sleeve (not shown) may be disposed within the first guide 333 and the second guide 334, respectively, and may be engaged with the posterior side of the glenoid 340.

Referring to FIGS. 3C and 3D, a first hole 349A and a second hole 349B may be formed through the glenoid, from the posterior side of the glenoid 340 to the anterior side 341 of the glenoid 340. According to one or more aspects, a drill (not shown) may be disposed within each of the first guide 333 and the second guide 334, shown in FIG. 3B, and may be advanced under power until the drill bit, e.g., drill bits 344A, 344B, exits the anterior edge/side 341 of the glenoid 340. As shown, the hooked end 331 of the glenoid guide (not shown) may provide a force in the posterior direction, i.e., in the direction of arrow W, while the drill bits 344A, 344B may be advanced in the anterior direction, i.e., in a direction that is opposite to the arrow W. According to one or more aspects, a 2.8 mm drill may be used to form the first hole 349A and the second hole 349B. However, those having ordinary skill in the art will appreciate that any size drill may be used to form the first hole 349A and the second hole 349B. According to one or more aspects, each of the first hole 349A and the second hole 349B may be 5 mm on center below a cortical edge of the glenoid face, and the holes 349A, 349B formed by the drill may be parallel to one another, and may be 10 mm apart, center to center. However, those having ordinary skill in the art will appreciate that each of the holes 349A, 349B may be formed more or less 5 mm, and may not necessarily be on center, below a cortical edge of the glenoid face. Further, those having ordinary skill in the art will appreciate that the holes 349A, 349B may be more or less than 10 mm apart, center to center. Furthermore, those having ordinary skill in the art will appreciate that more or less than two holes, e.g., the first hole 349A and the second hole 349B, may be formed in the glenoid 340.

For example, according to one or more aspects, one hole, or three holes, may be formed in glenoid 340, exiting the anterior side 341 of the glenoid 340.

Referring to FIG. 3E, according to one or more aspects, once forming the holes 349A, 349B is complete, the drill (not shown) may be removed from each of the guides (not shown), e.g., the guides 333, 334 of FIG. 3B, leaving the a first sleeve 335 and a second sleeve 336 in place within the body, engaged with the posterior side of the glenoid 340, and may correspond to the holes 349A, 349B formed on the anterior side/edge 341 of the glenoid 340. Further, the glenoid guide (not shown) may be removed. According to one or more aspects, a 1 mm pin may be disposed within each of the sleeves 335, 336 to ensure that the sleeves 335, 336 are free from debris. Those having ordinary skill in the art will appreciate that a member of any diameter, smaller or larger than 1 mm that is configured to be received by the sleeves 335, 336 may be used to remove debris from the sleeves 335, 336 and to ensure that each of sleeves 335, 336 is free from debris.

Referring to FIG. 3F, a first guidewire 311 and a second guidewire (not shown) may be disposed, or inserted, into the posterior portal, through the sleeves (not shown), e.g. the first sleeve 335 and the second sleeve 336 of FIG. 3E, respectively, and into the body. Further, an anterior portal (not shown) may be formed, and a first cannula 301 may be disposed, or inserted, into the body through the anterior portal. As shown, the first guidewire 311 may be disposed through the first sleeve and through the first hole 349A formed through the anterior side/edge 341 of the glenoid 340. Further, as shown, a grasper 360 may disposed into a proximal end (not shown) of the first cannula 301, may exit the first cannula at a distal end 306 of the first cannula 301, and may be used to engage, or retrieve, the first guidewire 311. According to one or more aspects, the grasper 360 may be used to pull each of the first guidewire 311 and the second guidewire out of the body, through the anterior portal, through the first cannula 301.

Referring to FIG. 3G, a bone block 310, according to embodiments disclosed herein, is shown. As shown, the bone block 310 may include a first hole 319A and a second hole 319B. As discussed above, each of the holes 319A, 319B may be configured to receive a first guidewire (not shown) and a second guide wire (not shown). Further, as discussed above, those having ordinary skill in the art will appreciate that the bone block 310 may be any bone block or bone graft that may be used in a surgical procedure. For example, in one or more embodiments, the bone block 310 may be used to treat anterior inferior glenohumeral instability within a body. Alternatively, the bone block 310 may be a bone block or bone graft of an appropriate size and shape, e.g. of appropriate dimensions, that may be used in a surgical procedure involving the shoulder, hip, knee, wrist, or ankle in a body. For example, according to one or more aspects, a tri cortical iliac crest bone block, measuring 20 mm×8 mm×8 mm may be harvested and fashioned using a graft preparation board. Further, according to one or more aspects, the holes 319A, 319B may be 2.8 mm in diameter and may be 10 mm apart, center to center. A drill may be used to form the holes 319A, 319B by entering through the cortex and exiting the cancellous side of the bone block 310. The holes 319A, 319B may be formed to correspond with the sleeves (not shown), e.g., sleeves 335, 336 placed in the glenoid, shown in FIG. 3E, and/or may be formed to correspond with the holes 349A, 349B formed in the glenoid 340, also shown in FIG. 3E. As discussed above, those having ordinary skill in the art will appreciate that more or less than two guidewires, e.g. guidewires 311, 312, may be used. For example, in one or more embodiments, one, three, four, or more guidewires may be used. Accordingly, those having ordinary skill in the art will also appreciate that more or less than two holes, e.g., holes 319A, 319B, may be formed through the bone block 310. For example, in one or more embodiments, one, three, four, or more holes may be formed through the bone block 310.

Referring to FIG. 3H, each of the guidewires 311, 312 may be pulled through the first cannula 301, exiting a proximal end 305 of the first cannula 301. Further, each of the guidewires 311, 312 may be disposed through each of the holes 319A, 319B of the bone block 310, respectively. According to one or more aspects, each of the guidewires 311, 312 may be inserted through the cancellous side of the bone block 310 and may exit through the cortical side of the bone block 310. According to one or more aspects, at least a portion of the guidewires 311, 312 may remain outside of the body, posteriorly, and may allow a surgeon to manipulate each of the guidewires 311, 312 posteriorly, while at least a portion of each of the guidewires 311, 312 is disposed within the body and/or is outside of the body on the anterior side.

Referring to FIGS. 3I and 3J, a first suture loop 321 having a first locking member 323 may be displaced, looped or passed, through the first loop 317 of the first guidewire 311, and also displaced, looped or passed, back through itself, in the direction of arrow D, in order to secure the first suture loop 321 and the first locking member 323 to the first loop 317 of the first guidewire 311. Similarly, as shown in FIG. 3J, the second suture loop 322 may be displaced, looped or passed, through the second loop 318 of the second guidewire 312, and also displaced, looped or passed, back through itself in order to secure the second suture loop 322 and the second locking member 324 to the second loop 318 of the second guidewire 312. Further, according to one or more aspects, each of the first suture loop 321 and the second suture loop 322 may be tensioned, e.g., in a direction substantially away from the first cannula 301, to secure the first suture loop 321 and the first locking member 323 to the first guidewire 311 and to secure the second suture loop 322 and the second locking member 324 to the second guidewire 312. As shown, each of the first locking member 323 and the second locking member 324 is resting against the bone block 310.

Referring to FIGS. 3K and 3L, multiple views of the surgical assembly 300, in accordance with embodiments disclosed herein, are shown. As shown, the bone block 310 may be disposed within the first cannula 301, through the proximal end 305 of the first cannula, and may be advanced into the body through the first cannula 301, through the anterior portal. According to one or more aspects, disposing the bone block 310 into the body may include pushing the bone block 310 into the body, through the first cannula 301, with an obturator 365. According to one or more aspects, disposing the bone block 310 into the body may include pulling the bone block 310 into the body, through the first cannula 301, with each of the first guidewire 311 and the second guidewire 312. According to one or more aspects, the first guidewire 311 and the second guidewire 312 may be used to reposition, or reorient, the bone block 310 such that the bone block 310 may be disposed within the first cannula 301 and displaced through the first cannula 301. For example, in one or more embodiments, the bone block 310 may be repositioned, or reoriented, by the first guidewire 311 and the second guidewire 312 such that a longitudinal axis of the bone block 310 is substantially parallel with a central axis 350 of the first cannula 301. Once the bone block 310 is fully inserted into the first cannula 301, the guide wires 311, 312 exiting the body, e.g. the shoulder, posteriorly may be tensioned to remove any slack in the guide wires 311, 312. According to one or more aspects, even if an obturator 365 is used to push the bone block 310 into the body through the first cannula 301, slight tension may be applied and/or maintained on the guidewires 311, 312, e.g., from the posterior side of the guidewires 311, 312.

As shown in FIG. 3L, the bone block 310 may exit the distal end 306 of the first cannula 301, inside the body, in a region of the body near the anterior edge/side 341 of the glenoid 340. As discussed above, in one or more embodiments, the obturator (not shown) may be used to push the bone block 310 into the body, toward the anterior edge/side 341 of the glenoid 340. Additionally, in one or more embodiments, the first guidewire 311 and the second guidewire 312, disposed through the holes 349A, 349B, respectively, may be used to apply and/or maintain slight tension on the bone block 310, as it is pushed into the body with the obturator. Alternatively, in one or more embodiments, the first guidewire 311 and the second guidewire 312, disposed through the holes 349A, 349B, respectively, may be used to pull the bone block 310 into the body, toward the anterior edge/side 341 of the glenoid 340, without the use of an obturator.

Referring to FIG. 3M, each of the guidewires (not shown), e.g. guidewires 311, 312 shown in FIG. 3L, disposed within sleeves 335, 336, may be pulled, or tensioned, posteriorly, and the bone block 310 may exit the distal end 306 of the first cannula 301, and may be manipulated, reoriented or repositioned, until it is placed in an intended position along the anterior neck of the glenoid 340. According to one or more aspects, the cancellous portion of the bone block 310 may be secured against the glenoid 340, e.g. a neck of the glenoid 340. Further, according to one or more aspects, a grasper (not shown), e.g., the grasper 360 shown in FIG. 3F, may be used to manipulate, reorient or reposition, the bone block 310 within the body, against the glenoid 340. During the placement of the bone block 310 within the body, slight tension may be maintained on each of the suture loops 321, 322, anteriorly, such that each of the first locking member 323 and the second locking member 324 are engaged with the bone block 310, while the guidewires 311, 312 may be pulled, posteriorly, to seat the bone block 310 on the glenoid 340.

Referring to FIGS. 3N and 3O, according to one or more aspects, each of the first suture loop 321 and the second suture loop 322 may be disengaged from the guidewires 311, 312, respectively, and may be removed from the body. As shown, a second cannula 302 may be disposed within the body, in addition to the first cannula 301, in the vicinity of the glenoid 340 and the bone block 310. According to one or more aspects, the first locking member 323 and the first suture loop 321 may be disengaged from the first guidewire 311 and removed from the body through the second cannula 302. According to one or more aspects, a grasper (not shown), e.g., the grasper 360 shown in FIG. 3F, may be disposed through the second cannula 302 used to remove the first locking member 323 and the first suture loop 321 from the body, while the second locking member 324 remains engaged with the bone block 310. As discussed above, in one or more embodiments, in order to remove, or disengage, the first suture loop 321 from the first guidewire 311, a surgeon may pull the first locking member 323 in a direction that is substantially away from the first guidewire 311. Pulling the first locking member 323 in a direction that is substantially away from the first guidewire 311 may cause the first suture loop 321 to become unraveled, or become un-looped, and disengage from the first guidewire 311.

Once the first locking member 323 and the first suture loop 321 are removed from the body, a needle guide wire 353 may be placed into the body, e.g., into a proximal end 307 of the second cannula 302 and may exit a distal end 308 of the second cannula 302, to create a subscapularis portal in-line with the holes of the bone graft 310, e.g., holes 319A, 319B of the bone graft 310 shown in FIG. 3G. According to one or more aspects, once in the joint, a cannulated obturator (not shown) and a fixation cannula (not shown) may be inserted over the needle guidewire 353. According to one or more aspects, tension may be applied, posteriorly, on the second guidewire 312 in order to help maintain security of, e.g., engagement of, the bone block 310 against the glenoid 340, as the first guidewire 311 is removed, anteriorly, through the second cannula 302.

Referring to FIGS. 3P-3R, the sleeve (not shown), e.g., the sleeve 335 aligned with the hole 349A of the glenoid 340 and engaged with the posterior side of the glenoid 340, may be removed to accommodate placement of a first fixation screw 351. According to one or more aspects, the first fixation screw 351 may be inserted into the proximal end 307 of the second cannula 302 and may be passed over the needle guidewire 353, through the second cannula 302, and may be driven into the body by a drill or a screwdriver 334 until the first fixation screw 351 is engaged with the bone block 310, and the bone block 310 is secured against the anterior side/edge 341 of the glenoid 340. Once the first fixation screw 351 is secured within the bone block 310 within the body, the needle guidewire 353 may be removed from the body.

Subsequently, according to one or more aspects, the second locking member 324 and the second suture loop 322 may be removed from the body through the first cannula 301 in the same fashion described above, with regard to the first locking member 323 and the first suture loop 321. According to one or more aspects, a second fixation screw 352 may be engaged with the bone block 310 such that the bone block 310 is secured against the glenoid 340 in the same fashion as described above, with regard to the first fixation screw 351. For example, the sleeve (not shown), e.g., sleeve 336 aligned with the hole 349B of the glenoid 340 and engaged with the posterior side of the glenoid 340, may be removed to accommodate placement of the second fixation screw 352. Further, the needle guidewire 353 may be disposed through the first cannula 302. Furthermore, according to one or more aspects, the second fixation screw 352 may be passed over the needle guidewire 353, through the first cannula 301, and may be driven into the body by a drill or a screw driver until the second fixation screw 352 is engaged with the bone block 310, and the bone block 310 is secured against the glenoid.

Those having ordinary skill in the art will appreciate that a manual screwdriver, a powered drill, or any means of securing a screw into a surface may be used to secure the first fixation screw 351 and the second fixation screw 352 through the bone block 310 and into the glenoid 340. Further, according to one or more aspects, each of the first fixation screw and the second fixation screw 352 may be 34 mm cannulated screws. However, those having ordinary skill in the art will appreciate that fixations screws of any size that are adapted to be used with the bone block 310 may be used. Further, those having ordinary skill in the art will appreciate that more or less than two guidewires, e.g.

guidewires 311, 312, may be used. For example, in one or more embodiments, one, three, four, or more guidewires may be used.

According to one or more aspects, bioabsorbable anchors may be placed away from the trajectory of the fixation screws 351, 352 along the anterior edge of the glenoid 340, between the glenoid 340 and the bone block 310. Further, according to one or more aspects, sutures may be passed through a labrum and capsule and secured over a top, e.g., a cortical surface, of the bone block 310.

A surgical kit, according to embodiments disclosed herein, may include a first cannula having a hole formed therethrough and configured to receive a bone block, a proximal end, a distal end, and a central axis defined therethrough, a first guidewire, a second guidewire, a first suture loop comprising a first locking member, and a second suture loop comprising a second locking member.

The kit may also include a glenoid guide having a hooked end, a second cannula having a hole formed therethrough, a proximal end, and a distal end, a grasper, an obturator, a needle guidewire, at least one threaded screw, wherein the at least one threaded screw is cannulated, and a drill configured to secure the at least one threaded screw into a bone.

Advantageously, embodiments disclosed herein may provide a surgical assembly, method, and kit that may simplify and improve a technique for treating anterior-inferior glenohumeral instability. As discussed above, pushing/pulling a bone block with graspers within the body and securing the bone block with a suture may be difficult, and as a result, time-consuming, for a surgeon. The use of at least one threaded screw to secure a bone block and the use of guide wires, suture loops, and locking members to manipulate and secure the bone block within the body may help a surgeon in treating anterior-inferior glenohumeral instability more quickly, precisely, and effectively.

In an alternate configuration, a surgical delivery apparatus includes a suture, and a locking component having a hole formed therethrough, in which the hole of the locking component is configured to receive the suture. In one or more embodiments, the suture may be disposed through the hole formed in the locking component. In one or more embodiments, the suture may be formed into a closed loop. In one more embodiments, a first knot and a second knot may be formed on the suture to form the suture into the closed loop. In one or more embodiments, at least a portion of each of the first knot and the second knot formed on the suture may be seated within the hole formed through the locking component.

Figure 4A:
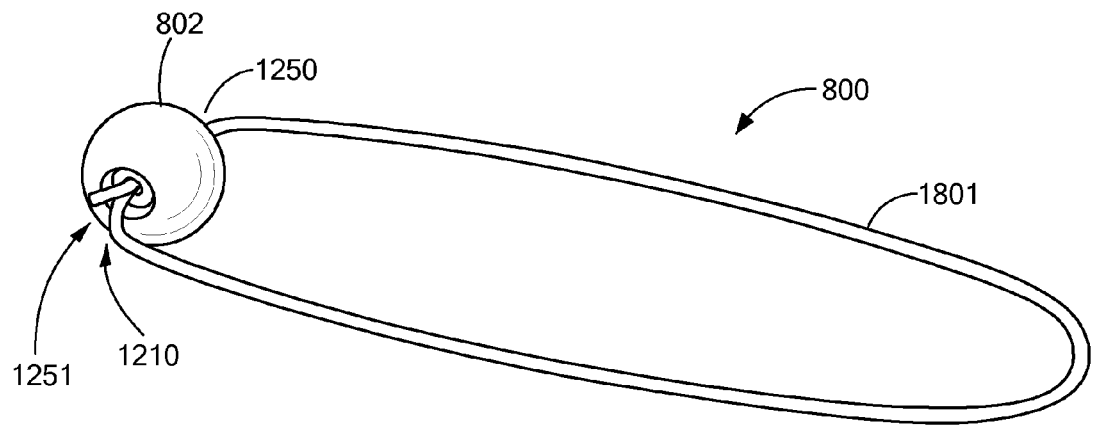
FIGS. 4A-4L show an alternate configuration having a suture loop 801 with a locking ball 802.

Referring to FIG. 4A, a surgical delivery apparatus 800, in accordance with embodiments disclosed herein, is shown. In one or more embodiments, the surgical delivery apparatus 800 may include a suture 801 and a locking component 802. In one or more embodiments, a hole 110 may be formed through the locking component 802, in which the hole 110 is configured to receive the suture 801. In one or more embodiments, the suture 801 may be disposed through the hole 110 formed through the locking component 802. In one or more embodiments, the locking component 802 may be coupled to the suture 801.

In one or more embodiments, the suture 801 may be formed from any flexible material known in the art, such as suture, polyester, plastic, a malleable metal, such as Nitinol, or any combination thereof. Further, as shown in FIG. 4A, the suture 801 may be formed into a closed loop. As used herein, the term "closed loop" may refer to any type of loop that is formed by the suture. In one or more embodiments, the suture 801 may be a closed, continuous loop. Alternatively, in one or more embodiments, each of the suture 801 may be closed and may contain one or more knots, e.g., first knot 107.

For example, in one or more embodiments, a first knot 107 and a second knot (not shown) may be formed on the suture 801 to form the suture 801 into a closed loop. Further, in one or more embodiments, movement of the locking component 802 along the suture 801 may be restricted by both the first knot 107 and the second knot formed on the suture. For example, in one or more embodiments, a circumference of each of the first knot 107 and the second knot may be larger than a diameter of the hole 110 formed through the locking component 802. Subsequently, in one or more embodiments, each of the first knot 107 and the second knot may not be able to pass freely through the hole 110 formed through the locking component 802. As such, in one or more embodiments, the locking component 802 may not be able to pass freely over either the first knot 107 or the second knot, which may restrict the movement of the locking component 802 along the suture 801. In one or more embodiments, at least a portion of each of the first knot 107 and the second knot may be seated within the hole 110 formed through the locking component 802. For example, as shown in FIG. 4A, at least a portion of the first knot 107 is seated, or disposed within, the hole 110 formed through the locking component 802.

As discussed above, in one or more embodiments, the locking component 802 may be coupled to the suture 801. Those having ordinary skill in the art will appreciate that the locking component 802 by any means known in the art. For example, the locking component 802 may be coupled to the suture 801 by mechanical or chemical means, such as crimping, molding, or gluing. Alternatively, as discussed above, in one or more embodiments, the locking component 802 may include the hole 110 formed therethrough, in which the locking component 802 may be threaded onto the suture 801, e.g., similar to a bead on a necklace. As shown, the locking component 802 is substantially spherical in shape.

Those having ordinary skill in the art will appreciate that the shape of the locking component 802 may be any shape known in the art. For example, the shape of the locking component 802 may be spherical, hemi-spherical, cubic, prismatic, pyramidal, T-bar-shaped, cylindrical, elliptical, hexagonal, or any other shape known in the art.

Further, in one or more embodiments, the locking component 802 may be formed from any material known in the art. For example, in one or more embodiments, the locking component 802 may be formed from metal, plastic, ceramic, or any other material known in the art. Alternatively, the locking component 802 may be formed form any biocompatible material known in the art. For example, in one or more embodiments, the locking component 802 may be formed from stainless steel.

According to another aspect, there may be provided a method for forming a closed loop for a surgical delivery apparatus, the method including providing a suture and a locking component, the locking component having a hole formed therethrough and is configured to receive the suture, disposing a first end of the suture through the hole formed through the locking component in a first direction, disposing a second end of the suture through the hole formed through the locking component in a second direction that is opposite to the first direction, forming a first knot on the suture with the first end of the suture, and forming a second knot on the suture with the second end of the suture.

The method may also include tightening the suture such that at least a portion of both the first knot and the second knot are seated within the hole formed through the locking component. The method may also include trimming the first end of the suture on a region of the suture near the first knot, and trimming the second end of the suture on a region of the suture near the second knot. According to one or more aspects, a trimming tool may be used to trim each of the first end and the second end of the suture, such that fraying of the suture does not occur as a result of the trimming.

Referring to FIGS. 4B-4L, a method of forming a loop for a surgical delivery apparatus 100, in accordance with embodiments disclosed herein, is shown. According to one or more aspects, the surgical delivery apparatus 100 may include a suture 801, having a first end 1205 and a second end 1206, and a locking component 802. According to one or more aspects, the locking component 802 may include a hole 210 formed therethrough.

Figure 4B:
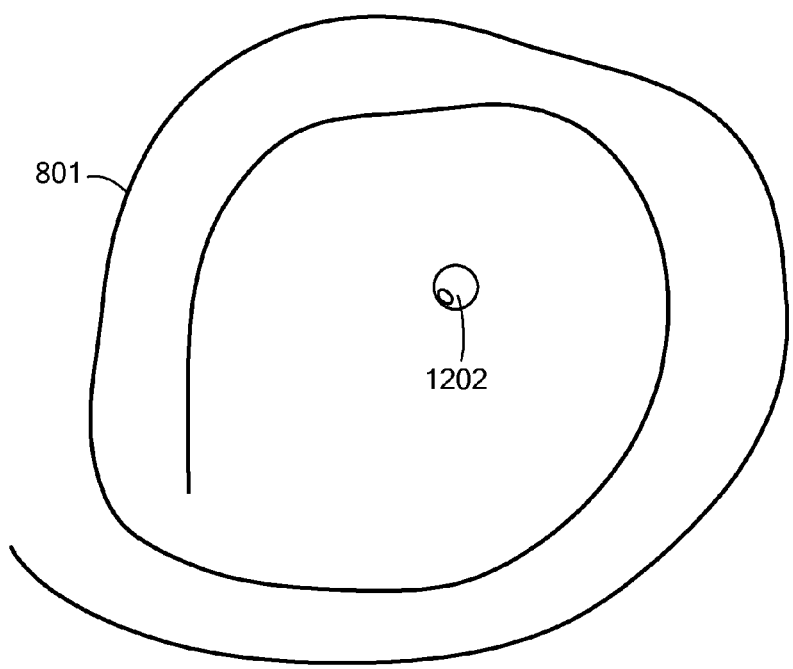
Figure 4C:
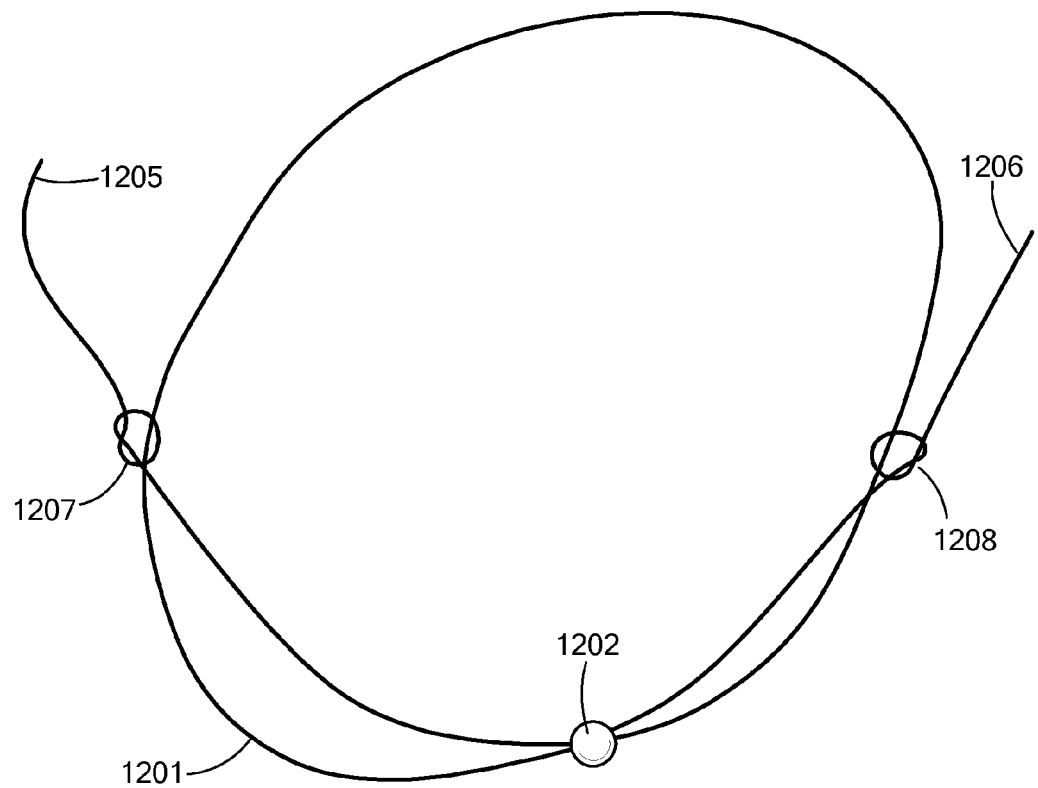

As shown in FIGS. 4A-4C the first end 205 of the suture 801 may be threaded, or disposed, through the hole 1210 of the locking component 802. According to one or more aspects, the first end 1205 of the suture 801 may be threaded, or disposed, through the hole 1210 of the locking component 802 in a first direction, such that the locking component 802 is threaded onto the suture 801, e.g., similar to a bead on a necklace.

Figure 4D:
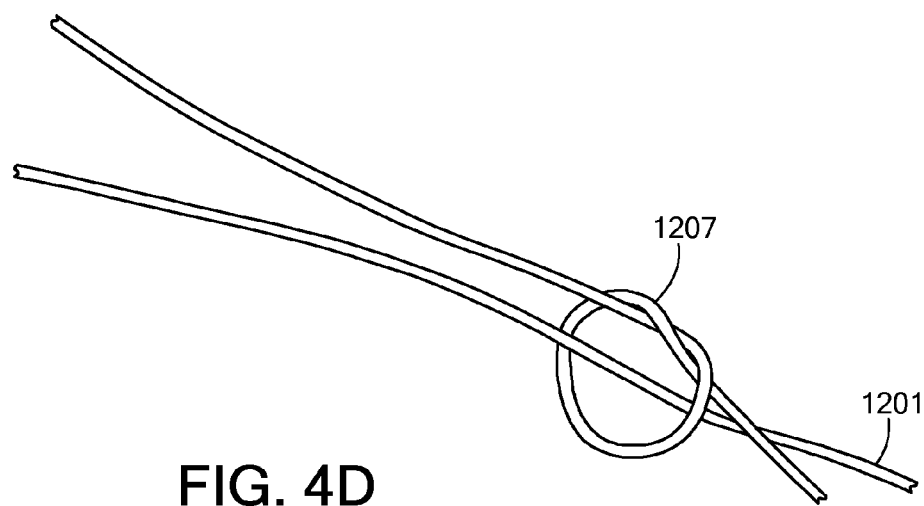
Figure 4E:
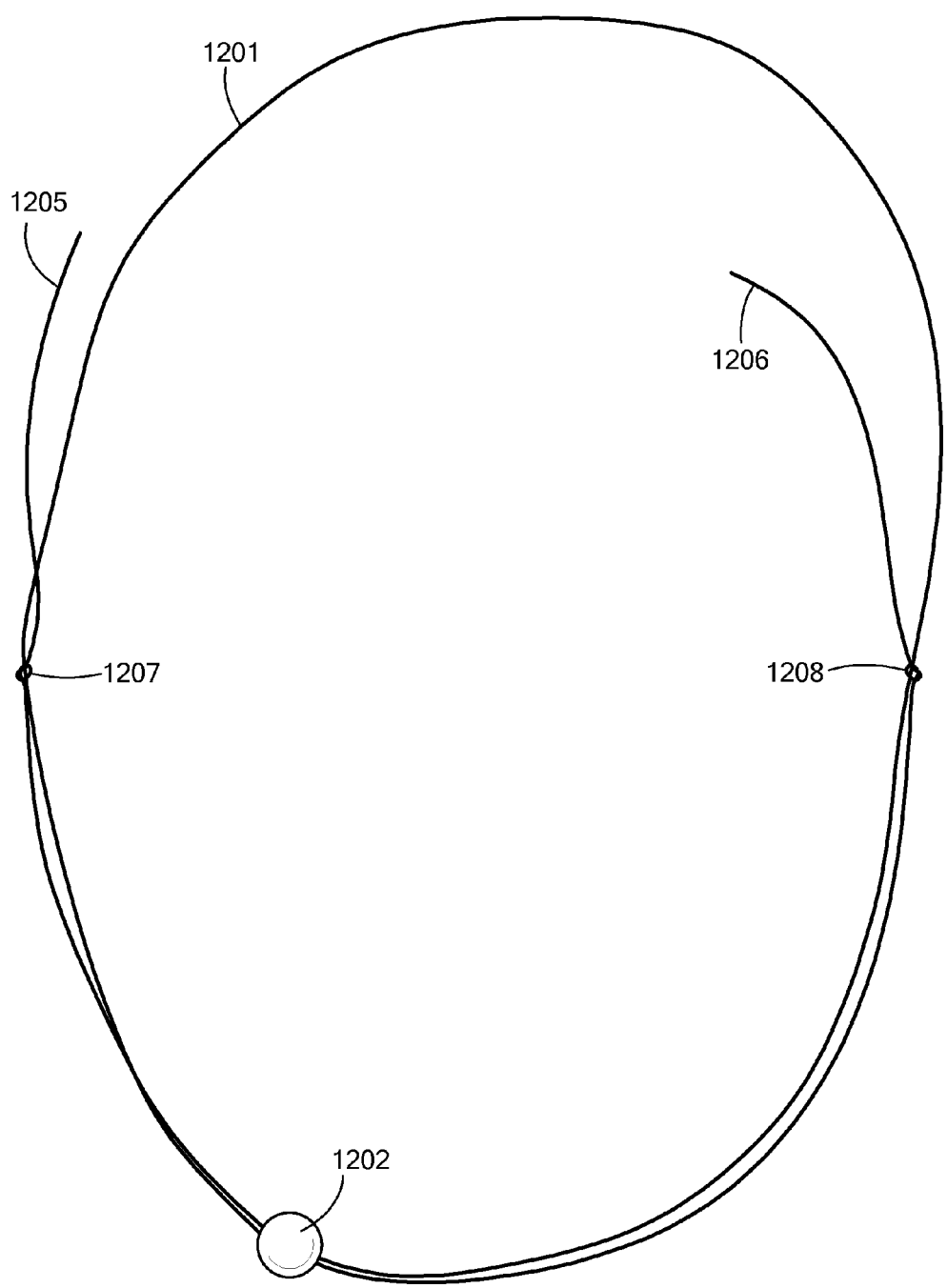

As shown in FIGS. 4D-4E, the second end 1206 of the suture 801 may be threaded, or disposed, through the hole 1210 of the locking component 802. According to one or more aspects, the second end 1206 of the suture 801 may be threaded, or disposed, through the hole 1210 of the locking component 802 in a second direction that is opposite to the first direction, described above with respect to the first end 1205 of the suture 801.

As shown in FIG. 4E, a first knot 1207 may be formed on the suture 801 using the first end 1205 of the suture 801, and a second knot 1208 may be formed on the suture 801 using the second end 1206 of the suture 801. According to one or more aspects, each of the first knot 1207 and the second knot 1208 may be overhand knots formed on the suture 801. Those having ordinary skill in the art will appreciate that other types of knots, other than an overhand knot, may be used to secure the first end 1205 of the suture 801 and the second end 1206 of the suture 801 to the suture 801. According to one or more aspects, 1-3 inches of the suture 801 may remain, regarding the first end 1205 and the second end 1206, once the first knot 1207 and the second knot 1208 have been tied. However, those having ordinary skill in the art will appreciate that, according to one or more aspects, more than 3 inches and less than 1 inch of the suture 801 may remain, regarding the first end 1205 and the second end 1206, once the first knot 1207 and the second knot 1208 have been tied.

Figure 4F:
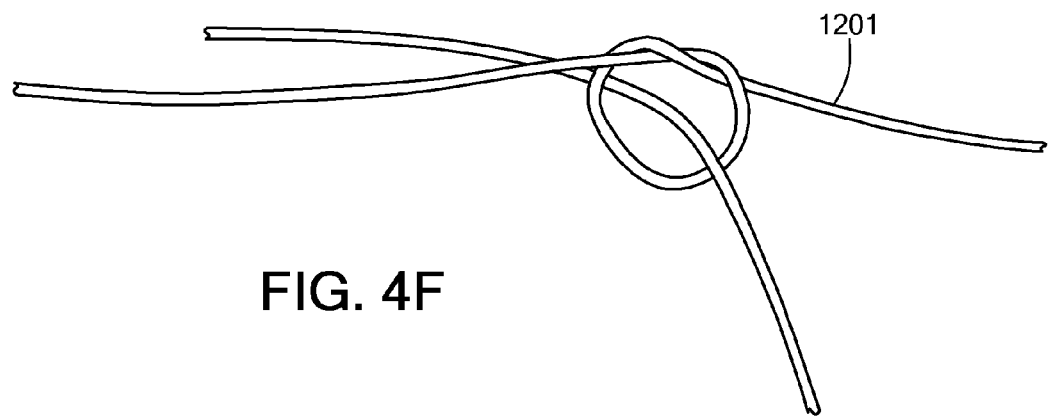
Figure 4G:
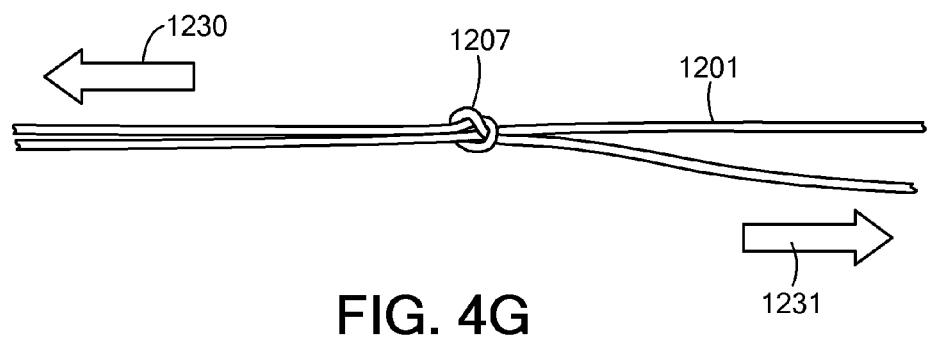
Figure 4H:
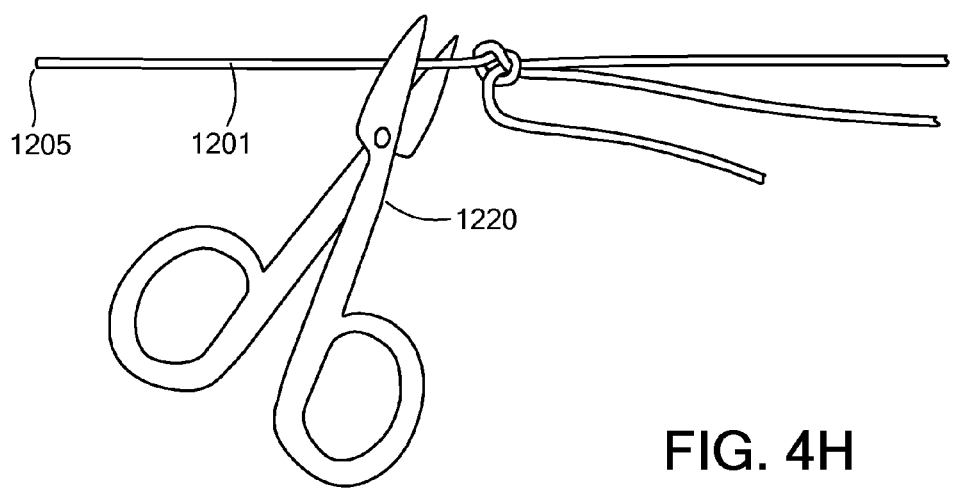
Figure 4I:
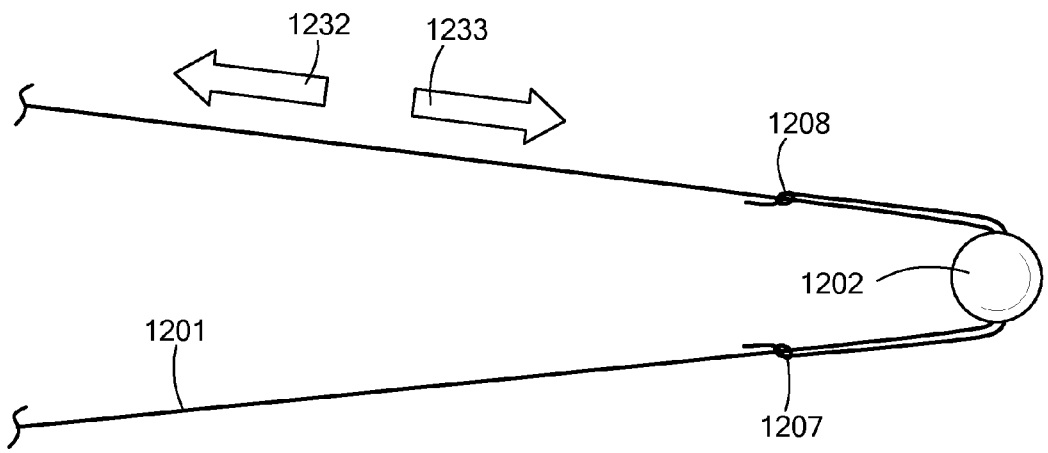
Figure 4J:
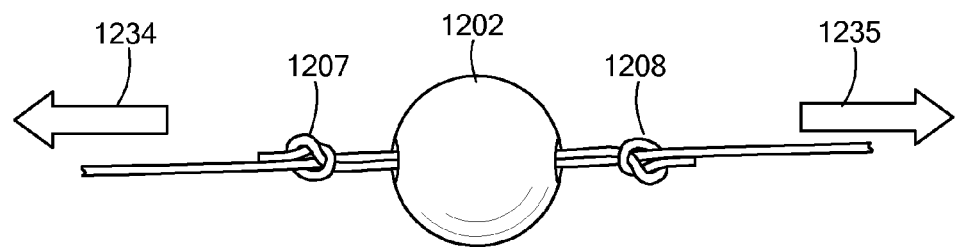
Figure 4K:
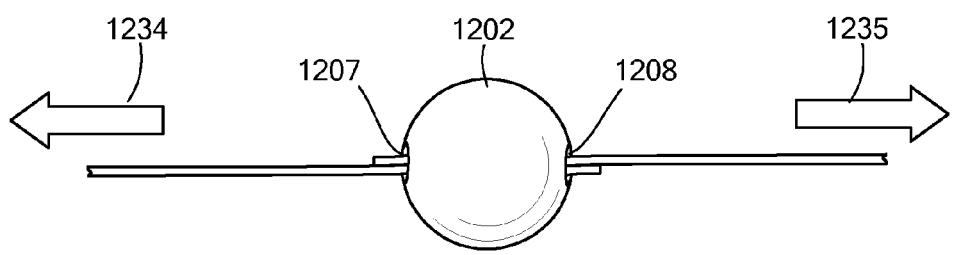
Figure 4L:
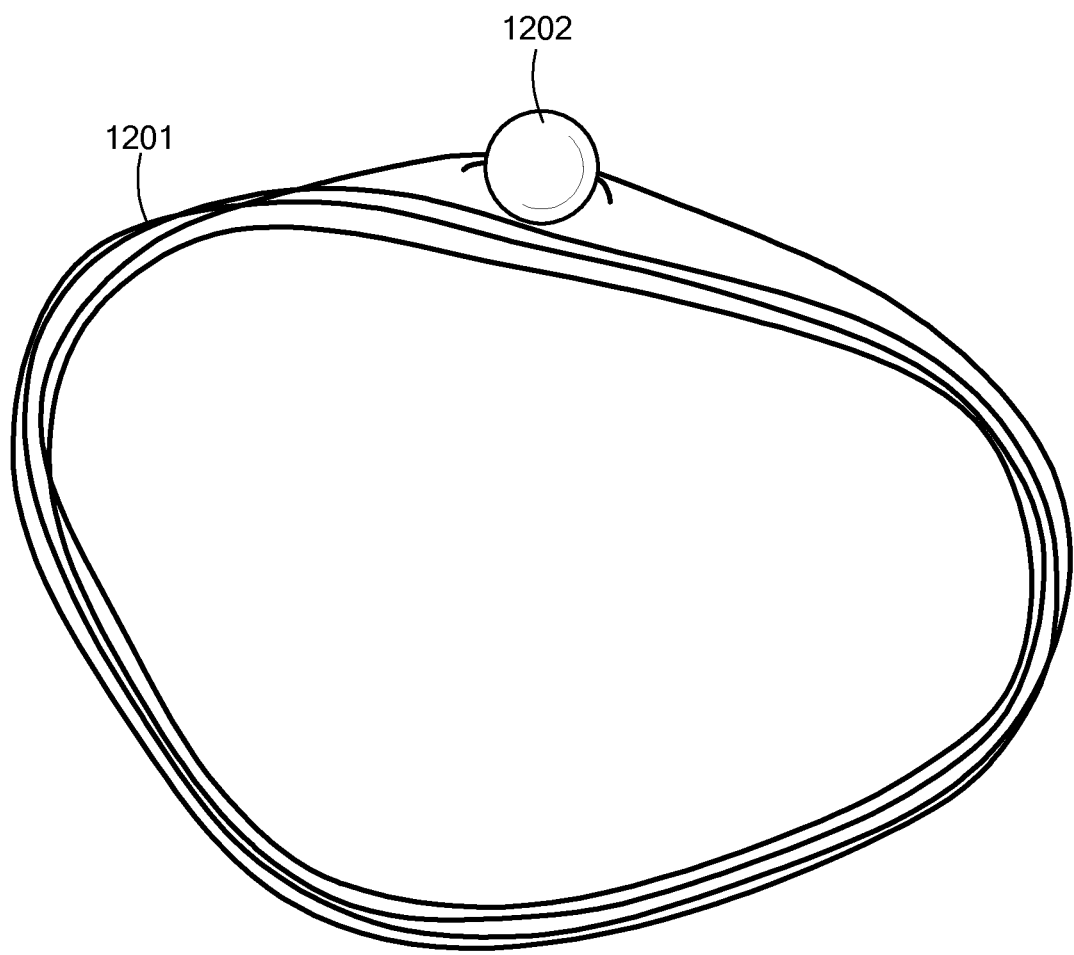
Figure 5A:
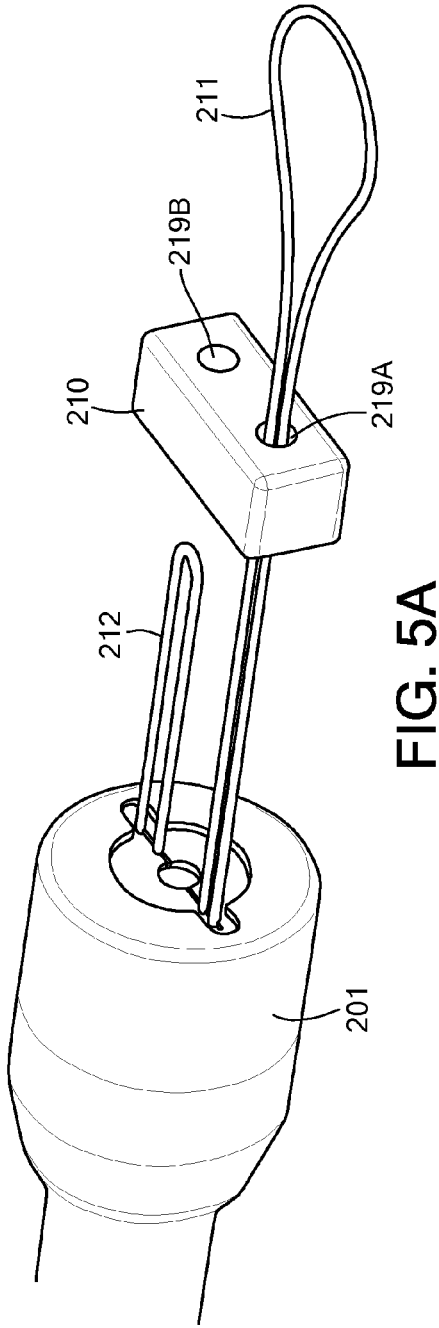
FIGS. 5A-5D depict bone graft mounting using the locking ball 802 arrangement of FIGS. 4A-4L.
Figure 5B:
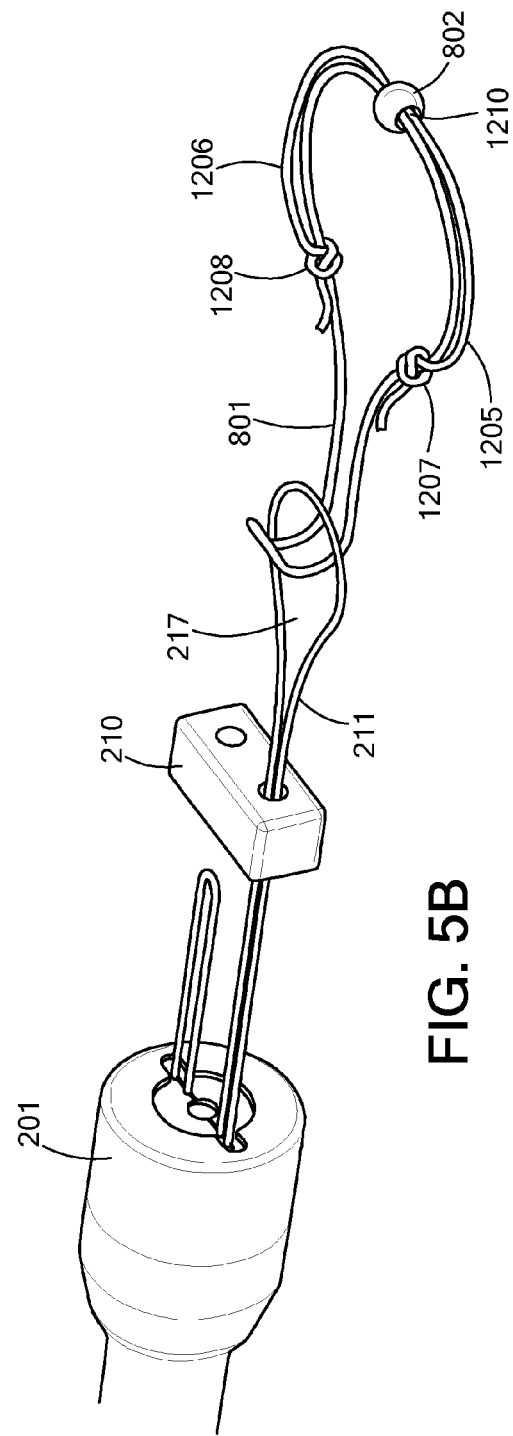
Figure 5C:
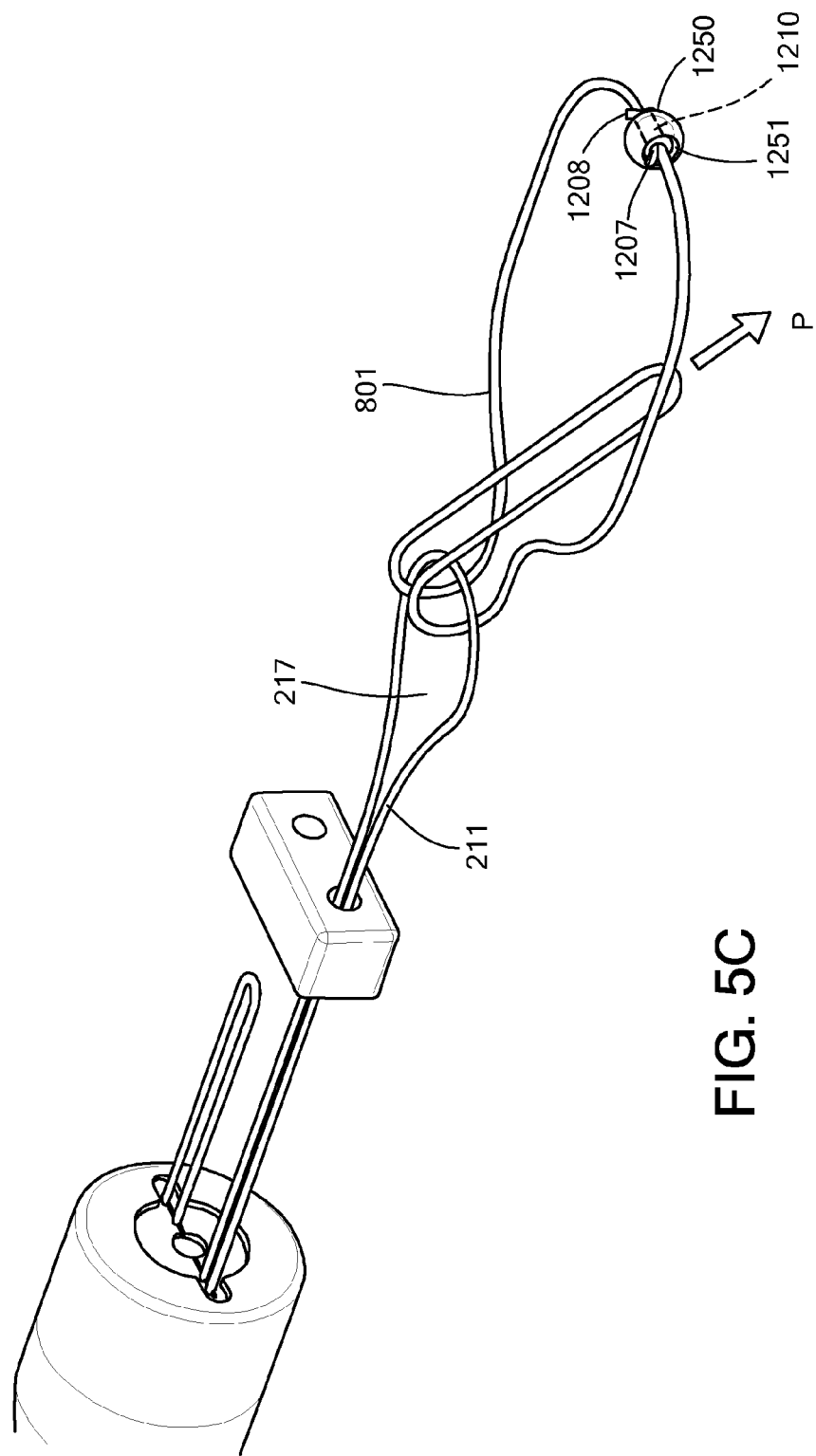
Figure 5D:
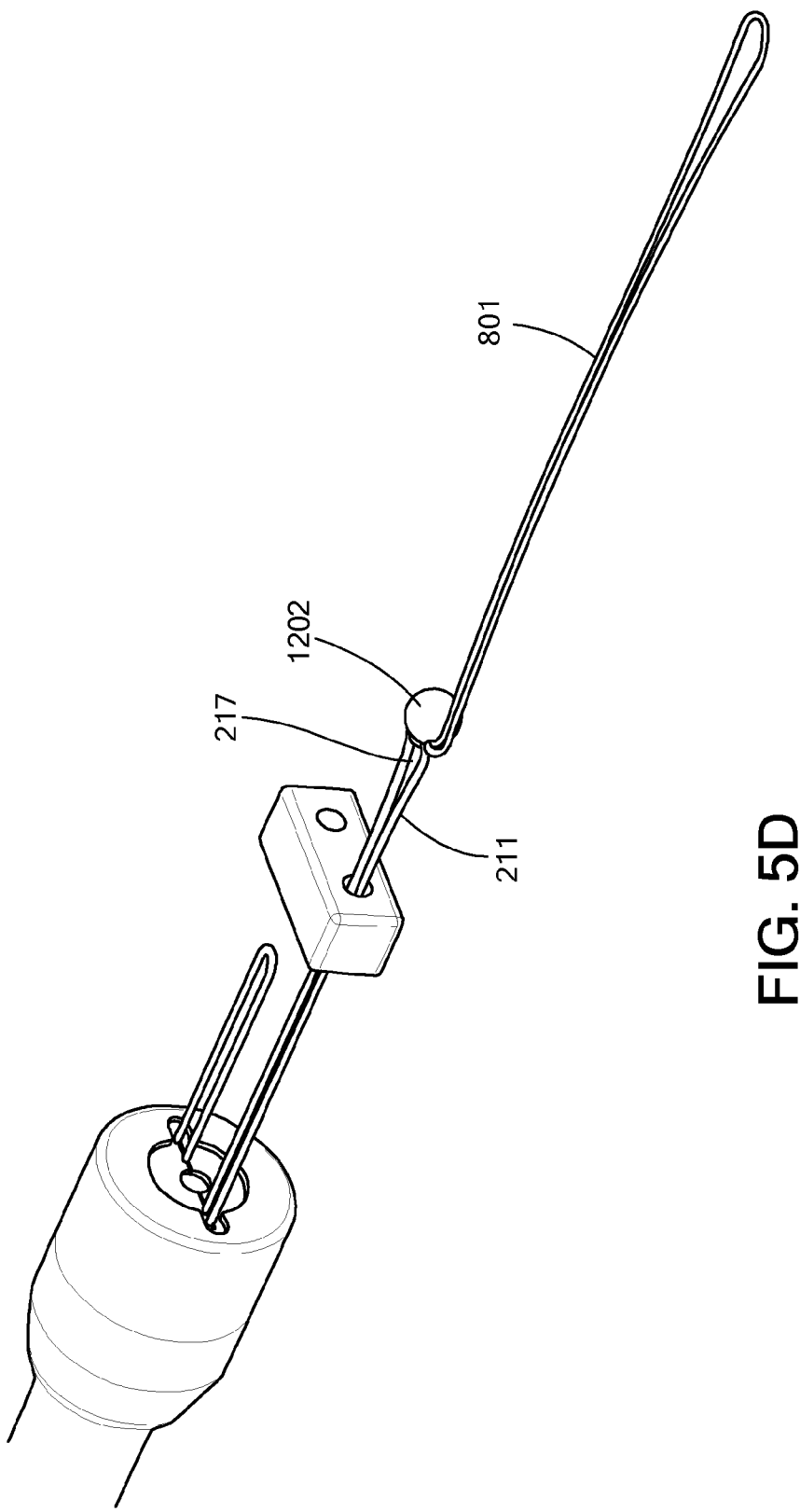

As shown in FIGS. 4F-4G, each of the first knot 1207 and the second knot (not shown) may be tightened. As shown, segments of the suture 801 on opposite sides of the knot 1207 may be pulled in the directions specified by arrows 1230 and 1231, respectively, to tighten the knot 1207. Those having ordinary skill in the art will appreciate that substantially the same measures may be taken to tighten the second knot.

As shown in FIG. 24H, each of the first end 1205 and the second end (not shown) may be trimmed using a trimming tool, such that fraying does not occur as a result of the trimming. As used herein, "fraying" may refer to an area of the suture 801 whose ends split up and become unraveled or distributed. Those having ordinary skill in the art will appreciate that the trimming tool may be any trimming tool known in the art. For example, according to one or more aspects, the trimming tool may be scissors, a knife, or any other object or tool with a sharp edge capable of severing, cutting, or trimming the suture 801. According to one or more aspects, a heated knife may be used as the trimming tool. According to one or more aspects, the heated knife may both sever, or trim, the suture 801 and may also close, e.g., melt, the trimmed areas of the suture 801 to prevent fraying. According to one or more aspects, 1 mm-3 mm of the suture 801 may remain of each of the first end 1205 and the second end 1206 after each end is trimmed. However, those having ordinary skill in the art will appreciate that more than 3 mm and less than 1 mm of the suture 801 may be left after each of the first end 1205 and the second end 1206 of the suture 801 is trimmed.

As shown in FIGS. 4I-4L, the suture 801 may be tightened, or tensioned, such that at least a portion of both the first knot 1207 and the second knot 1208 are seated, or disposed, within the hole formed through the locking component 802. As shown in FIG. 2L, segments of the suture 801 may be pulled, or tensioned, in the directions specified by arrows 1232 and 1233 to displace each of the first knot 1207 and the second knot 1208 toward the locking component 802. Further, as shown in FIGS. 2M-2N, segments of the suture 801 may be further pulled, or tensioned, in the directions specified by arrows 1234 and 1235 to further displace each of the first knot 1207 and the second knot 1208 toward the locking component 802. According to one or more aspects, the segments of the suture 801, discussed above, may be on either side of the locking component 802. According to one or more aspects, a first segment of the suture 801 may be pulled in the direction of arrow 1234 and a second segment of the suture 801, which is on an opposite side of the locking component 802 from the first segment, may be pulled in the direction of arrow 1235, which may cause tension on the suture 801.

Advantageously, embodiments disclosed herein may provide a surgical delivery apparatus and a method of forming a loop for a surgical delivery apparatus that may simplify and improve a technique for treating anterior-inferior glenohumeral instability. As discussed above, forming a first knot and a second knot on opposite sides of a locking component may restrict movement of the locking component along a suture. Restricting this type of movement on the suture may help during installation and retrieval of the surgical delivery device by a surgeon in treating anterior-inferior glenohumeral instability more quickly, precisely, and effectively.

FIGS. 5A-5D show an alternate configuration having a suture loop 801 with a locking ball 802, similar to the locking component 124 shown in FIGS. 3A-3R. FIGS. 5A-5D depict bone graft mounting using the locking ball 802 arrangement of FIGS. 4A-4L. Referring to FIGS. 1 and 5A-5D the first guidewire 211 engages a suture 801 having a placement object 802, such as a locking component 124. The locking 802 has a bore 1210 extending therethrough at a width adapted for receiving a plurality of sutures. The suture 801 has a first end 1205 and a second end 1206 both passed through the bore 1210 in the placement object 802. The opposed ends 1205, 1206 are tied in respective knots 1207, 1208 on the suture 801 to form a continuous loop. The ends 1206 and 1206 may be trimmed beyond the knots 1207, 1208 to any suitable length. The suture 801 is then drawn to slideably dispose the knots 1207-1208 toward the placement object 802 such that the knots 1207, 1208 are concealed in counterbores 1251, 1250, respectively. The knots 1207, 1208 are of a diameter that they cannot pass beyond the counterbore 1250, 1250 into the bore 1210, and therefore prevent sliding of the placement object 802 and allow manipulation of the placement object 802 via tension on the suture 801. The placement object 802 therefore engages the first or second guidewire 211, 212 as above for facilitating bone graft 110 placement while permitting tensioned control from the suture 801.

In the example configuration and procedure depicted in FIGS. 5A-5D, the bone graft placement device 800 includes a placement object 802 having an exterior surface, such that the exterior surface is adapted for engaging a bone graft 210 and distributing forces across a surface of the bone graft 210 for disposing the bone graft 210 into alignment with a receptive surgical site 340. An aperture through the exterior surface defines a bore 1210 receptive to the suture 801 for securing the suture 801 for drawing the placement object 802 against the bone graft 210 for disposing the bone graft 210 to the surgical site. In the example arrangement, the placement object 802 is spherical and the aperture is defined by the bore 1210 through the sphere and adapted to pass at least one suture through the bore, such that the bore 1210 defines an aperture on both sides of the placement device in which the suture 801 emanates from both apertures.

In operation, the method of placing the surgical bone graft 210 includes engaging the bone graft 210 with the placement object 802, such that the placement object 802 disposes the bone graft 210 into alignment with predrilled apertures 349A, 349B by evenly distributing forces on the bone graft 210. The placement object 802 disposes the bone graft 210 from an external tethered linkage provided by the guide wire 211, such that the tethered linkage secures the placement object 802 and is responsive to tension forces external to the arthroscopic surgical site due to the tethered linkage engaging a suture strand 801 passing through the placement object 802. Tension or pulling on the guide wire 211 therefore guides the bone graft 210 to a predetermined position at the surgical site by disposing the bone graft 210 via the tether, due to the tether passing through an engagement surface 340 receptive to the bone graft. A plurality of guide holes on the engagement surface may be employed, such that each of the plurality of guide holes corresponds to a hole on the bone graft, each of the corresponding pairs of holes for receiving the threaded tether for guiding a respective placement object.

Proper preparation includes forming the bore 1210 through the placement object 802, and forming a continuous suture loop 801 passed through the bore 1210 in the placement object 802. The formed bore 1210 has a width of at least two sutures, as the continuous suture loop 801 is formed passing a plurality of suture strands 801 through the bore, one end in each direction, and engaging the passed strand with an adjacent strand of the passed plurality of strands. Preparation includes passing the opposed ends 1205, 1206 of the suture strand 801 through the bore 1210, in which the opposed strands enter the bore from opposed ends such that the passed strands form a loop closed by adjacent strands passing in the bore. In the example arrangement, both ends 1205 and 1206 of the suture strand 801 are inserted into opposite ends (apertures) of the bore 1201, passing in opposite directions and emerging on the opposed sides. The loop 801 is closed by attaching each end of the opposed strands to the adjacent strand upon exiting the bore by knots 1207, 1208.

In a particular arrangement, this includes inserting first and second ends 1205, 1206 of a suture strand 801 through opposed ends of the bore 1210, in which each inserted end defines a trailing suture segment and passing the other of the first 1205 and second ends 1206 within the bore 1210. The suture slideably engages each of the first 1205 and second ends 1206 with the trailing suture segment of the other of the first and second end by knotting the end to the trailing suture segment, such that the knot 1207, 1208 is adapted to slide along the trailing suture segment to the bore 1210 for drawing the suture down to the knot 1207, 1208. Counterbores 1250, 1251 conceal the knots 1207, 1208 flush with the external surface of the placement object 802 and fix the suture 801 as the knot is larger than the bore 1210 beyond the recess of the counterbore 1250, 1251.

The surgical procedure may further include identifying the engagement surface on a skeletal member of a patient, drilling a plurality of guide holes 349A, 349B through the engagement surface, and threading a tether such as the guide wire 311 through each of the guide holes 349A, 349B. A surgeon then positions a placement tube to define the predrilled apertures, and passes the tether through the placement tubes, the predrilled apertures and the aperture in the placement object 802.

In the example arrangement, the surgical delivery apparatus 800 includes a suture 802, and a locking component such as the placement object 802 having a hole formed therethrough such as bore 1210. In keeping with the surgical nature, the locking component is substantially spherical in shape and comprises a biocompatible material. The hole of the locking component is configured to receive the suture 801, responsive to the suture 801 being disposed through the hole formed through the locking component and formed into a closed loop. A first knot and a second knot are formed on the suture to form the suture into the closed loop, and movement of the locking component along the suture 801 is restricted by both the first knot and the second knot formed on the suture. At least a portion of each of the first knot 1207 and the second knot 1208 formed on the suture are seated within the hole 1210 formed through the locking component.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical delivery apparatus comprising:
   a suture; and
   a locking component having a hole formed therethrough, wherein the hole of the locking component is configured to receive the suture, and wherein the suture is disposed through the hole formed through the locking component and formed into a closed loop which extends a distance away from and loops back to the locking component,
   wherein an end of the closed loop distal from the locking component is threaded through a receiving guidewire loop and then back through itself to join the surgical delivery apparatus with the receiving guidewire loop, whereby the locking component is positioned at the intersection point between the receiving guidewire loop and the closed loop of the surgical delivery apparatus,
   wherein pulling the locking component disengages the surgical delivery apparatus from the receiving guidewire loop.

2. The apparatus of claim 1, wherein a first knot and a second knot are formed on the suture to form the suture into the closed loop.

3. The apparatus of claim 2, wherein movement of the locking component along the suture is restricted by both the first knot and the second knot formed on the suture.

4. The apparatus of claim 3, wherein at least a portion of each of the first knot and the second knot formed on the suture are seated within the hole formed through the locking component.

5. The apparatus of claim 1, wherein the locking component is substantially spherical in shape and comprises a biocompatible material.

6. The apparatus of claim 1, wherein the closed loop is formed by threading a first end of the suture through the hole in the locking component in a first direction and a second end of the suture through the hole in the locking component in a second opposite direction and knotting the first and second threaded ends to the closed loop on respective sides of the locking component to form knots.

7. The apparatus of claim 6, wherein the forming of the closed loop further includes trimming the ends of the suture after the knotting thereof.

8. The apparatus of claim 6, wherein the forming of the closed loop further includes pulling the loop taut such that that the knots are seated or disposed, within the hole.

9. The apparatus of claim 8, wherein movement of the locking component along the suture is restricted by the knots.

10. The apparatus of claim 1, wherein the closed loop extends away from a first end of the hole in the locking component and loops back around to a second opposite end of the hole in the locking component.

* * * * *